US009717916B2

(12) United States Patent
Ortega et al.

(10) Patent No.: US 9,717,916 B2
(45) Date of Patent: *Aug. 1, 2017

(54) SYSTEM FOR DETERMINATION AND UTILIZATION OF CARDIAC ELECTRICAL ASYNCHRONY DATA

(71) Applicant: XSynchro, Inc., Bradenton, FL (US)

(72) Inventors: Daniel Felipe Ortega, San Fernando (AR); Julio César Spinelli, Bradenton, FL (US); Maria Paula Bonomini, Buenos Aires (AR); Luis Dante Barja, Belen de Escobar (AR)

(73) Assignee: XSynchro, Inc., Villa Martelli (AR)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,254

(22) Filed: Jul. 18, 2016

(65) Prior Publication Data

US 2016/0325097 A1     Nov. 10, 2016

Related U.S. Application Data

(63) Continuation of application No. 14/433,372, filed as application No. PCT/US2013/063130 on Oct. 2, 2013, now Pat. No. 9,392,949.

(Continued)

(51) Int. Cl.
*A61B 5/04*      (2006.01)
*A61N 1/365*     (2006.01)
(Continued)

(52) U.S. Cl.
CPC ............ *A61N 1/3682* (2013.01); *A61B 5/042* (2013.01); *A61B 5/04011* (2013.01);
(Continued)

(58) Field of Classification Search
None
See application file for complete search history.

(56) References Cited

U.S. PATENT DOCUMENTS

| 6,978,184 B1 | 12/2005 | Marcus et al. |
| 2006/0167364 A1 | 7/2006 | Houben |

(Continued)

FOREIGN PATENT DOCUMENTS

| EP | 1038498 | 9/2000 |
| EP | 2030564 | 3/2009 |

OTHER PUBLICATIONS

Porciani et al., "Utility of a New Left Ventricular Asynchrony Index as a Predictor of Reverse Remodelling After Cardiac Resynchronization Therapy." (Jan. 2006).

*Primary Examiner* — Brian T Gedeon
(74) *Attorney, Agent, or Firm* — Patrick J. S. Inouye; Leonid Kisselev

(57) ABSTRACT

One embodiment provides a system for determination and utilization of cardiac electrical asynchrony data. The system includes an analysis circuitry including a processor and a memory, the analysis circuitry configured to: obtain a plurality of sets of cardiac signals collected in at least two locations of a heart of a patient, the signals comprising at least one of surface electrocardiography signals and pseudo-surface ECG signals; detect one or more QRS complexes for each of the sets based on the cardiac signals for that set; obtain one or more cross-correlation signals, each of the cross-correlation signals being between at least two of the signal sets and being obtained using the detected QRS complexes from the signal sets; and calculate one or more asynchrony indices using one or more of the cross-correlation signals, each of the asynchrony indices being indicative of a level of asynchrony between the at least two locations.

20 Claims, 33 Drawing Sheets

Multilead Approach – Signal Preprocessing

Related U.S. Application Data

(60) Provisional application No. 61/708,992, filed on Oct. 2, 2012.

(51) Int. Cl.

| | | |
|---|---|---|
| *A61N 1/05* | (2006.01) | |
| *A61B 5/0428* | (2006.01) | |
| *A61B 5/0472* | (2006.01) | |
| *A61N 1/368* | (2006.01) | |
| *A61N 1/372* | (2006.01) | |
| *A61B 5/042* | (2006.01) | |
| *A61B 5/0456* | (2006.01) | |

(52) U.S. Cl.
CPC ...... *A61B 5/04012* (2013.01); *A61B 5/04017* (2013.01); *A61B 5/0428* (2013.01); *A61B 5/0456* (2013.01); *A61B 5/0472* (2013.01); *A61N 1/056* (2013.01); *A61N 1/3684* (2013.01); *A61N 1/3688* (2013.01); *A61N 1/36514* (2013.01); *A61N 1/36542* (2013.01); *A61N 1/36564* (2013.01); *A61N 1/36585* (2013.01); *A61N 1/37252* (2013.01)

(56) References Cited

U.S. PATENT DOCUMENTS

| | | |
|---|---|---|
| 2006/0271119 A1 | 11/2006 | Ni |
| 2008/0294218 A1 | 11/2008 | Savage et al. |
| 2009/0105556 A1 | 4/2009 | Fricke et al. |
| 2011/0257696 A1 | 10/2011 | Holmstrom et al. |
| 2012/0004564 A1 | 1/2012 | Dobak |
| 2012/0035678 A1 | 2/2012 | Joo et al. |
| 2012/0053470 A1 | 3/2012 | Wong et al. |
| 2012/0059272 A1 | 3/2012 | Blomqvist |
| 2012/0101539 A1 | 4/2012 | Zhu et al. |

SYSTEM FOR DETERMINATION AND UTILIZATION OF CARDIAC ELECTRICAL ASYNCHRONY DATA

RELATED DOCUMENTS

This non-provisional patent application is a continuation of U.S. Pat. No. 9,392,949, issued Jul. 19, 2016, which is a national stage entry of PCT Application Serial No. PCT/US/2013/063130, which claims benefit under 35 U.S.C. §119 to U.S. Provisional Patent Application Ser. No. 61/708, 992, entitled "Ventricular Pacing in Cardiac-Related Applications" and filed on Oct. 2, 2012, which, along with the Appendices and any cited references therein, is fully incorporated herein by reference.

SUMMARY

Various aspects of the present disclosure are directed toward use of an asynchrony index that is related to data of a subject's heart, for instance, in which the asynchrony index relates to or includes intra-ventricular or inter-ventricular electrical asynchrony data, and data associated with cardiac/physiological conditions. The intra-ventricular or inter-ventricular electrical asynchrony data can be specific to a certain subject, and indicative of different conditions specific to that subject. As discussed below, the asynchrony index provides data sets for the different subject-specific conditions, spanning a range of uses and implementations.

In certain embodiments, apparatuses and methods are directed toward use with a subject's cardiac data, corresponding to an electrocardiogram (ECG) or pseudo-surface ECG. The apparatuses include a first and/or second circuit that store an asynchrony index in which sets of intra-ventricular or inter-ventricular electrical asynchrony data are provided for the subject's heart. The sets respectively correspond to different conditions that are specific to the subject. Additionally, the first and/or second circuits provide access to at least one of the sets of intra-ventricular or inter-ventricular electrical asynchrony data. This occurs in response to an input signal that targets a specific portion of the asynchrony index or otherwise identifies one of the different conditions that are specific to the subject (or a corresponding one of the sets of intra-ventricular or inter-ventricular electrical asynchrony data). In one method relating thereto, a subject's cardiac data (corresponding to an electrocardiogram (ECG) or pseudo-surface ECG) is collected and organized, e.g., in the form of a table, with sets of intra-ventricular or inter-ventricular electrical asynchrony data that are specific to the subject's heart; the collected and organized cardiac data can also include and/or be correlated to different conditions that are specific to the subject.

Certain other embodiments of the present disclosure are directed toward apparatuses and methods that include an acquisition circuit that collects a first signal at a first location of a subject's heart and a second signal at a second location of the subject's heart. The first signal is indicative of at least one of a first heart surface electrocardiography (ECG) and a first intracardiac electrogram (EG). The second signal is indicative of at least one of a second heart surface ECG and a second intracardiac electrogram (EG). The apparatuses also include preprocessing circuitry that performs detection and filtering of QRS complexes of the first signal and the second signal collected by the acquisition circuit. Further, the apparatuses include analysis circuitry that extracts signal information including parameters or data points from the first signal and the second signal. Additionally, the analysis circuitry segments the QRS complexes of the first signal and the second signal using the extracted information. Further, the analysis circuitry cross-correlates the QRS complex segments of the first signal and the second signal to produce a correlation signal, and provides or calculates an asynchrony index that is based on or corresponds to the correlation signal and that indicates a level of electrical asynchrony between the first location and the second location.

Yet other embodiments are directed toward various methods for using and generating asynchrony index data as described in connection with one or more of the above apparatuses and/or methods of use.

Aspects of the present disclosure are also directed toward a dedicated device to assess the degree of inter and intra-ventricular electrical asynchrony (IEA) to determine the need for resynchronization therapy. Further, various aspects of the present disclosure are directed toward evaluation, during the implant procedure, to determine the correct location of the stimulation lead(s), and the optimization of the post implant outcome, non-invasively using two or more leads of the surface ECG. Moreover, certain aspects of the present disclosure are directed toward finding and initially programming into the device, the optimum atrio-ventricular interval that minimizes IEA, and finding and initially programming the interventricular interval that minimizes IEA in single and/or multiventricular stimulation systems.

Various aspects of the present disclosure are also directed toward a device and process that allows the continuous optimization of the auriculo ventricular interval and the inter ventricular interval in multichamber and/or multisite stimulation devices by reprogramming those parameters using electrocardiograms derived from intracardiac ECGs using a combination of the stimulation electrodes with the stimulation device. Other aspects of the present invention are directed toward the chronic optimization of the atrio-ventricular interval and the inter ventricular interval in multichamber and/or multisite stimulation devices by communicating automatically with the programmer and then reprogramming the device automatically, or with medical personnel intervention, to confirm/approve the new settings recommended by the optimization process, with this process taking place either at each follow up visit or at the home of the patient through a remote patient monitoring and/or management system. The invention also describes the use of the same method to optimize the lead position and initial atrioventricular delay in patients who are undergoing a right ventricular only implantation of a pacemaker. In still other aspects of this invention it describes a method and apparatus that allows the optimization of the atrio-ventricular interval and the inter ventricular interval (VV) in multichamber and/or multisite stimulation devices by communicating automatically with the programmer and then reprogramming the device automatically or with medical personnel intervention to confirm/approve the new settings recommended by the optimization process, with this process taking place either at each follow up visit or at the home of the patient through a remote patient monitoring and/or management system.

One embodiment provides a system for determination and utilization of cardiac electrical asynchrony data. The system includes an analysis circuitry including a processor and a memory, the processor configured to execute computer-executable code stored in the memory, the analysis circuitry configured to: obtain a plurality of sets of cardiac signals collected in at least two locations of a heart of a patient, the signals comprising at least one of surface electrocardiography signals and pseudo-surface ECG signals; detect one or more QRS complexes for each of the sets based on the cardiac signals for that set; obtain one or more cross-correlation signals, each of the cross-correlation signals being between at least two of the signal sets and being obtained using the detected QRS complexes from the at least two signal sets; and calculate one or more asynchrony indices using one or more of the cross-correlation signals, each of the asynchrony indices being indicative of a level of asynchrony between the at least two locations.

INTRODUCTION

Pacing in right ventricular apex causes intra and inter ventricular electrical asynchrony (WA) in roughly fifty percent of the patients that are paced in the right ventricle. Naturally occurring left bundle branch block (LBBB) also deteriorates ventricular function by creating, in many instances, an even worse type of ventricular asynchrony than RV apex pacing. IEA has been associated in the literature with an acceleration in the progression of heart failure and/or with a higher likelihood of developing heart failure (HF). With the idea of improving electrical asynchrony, especially in patients with heart failure, in recent years two lines of research have been pursued, one of them tries to resynchronize both ventricles, placing an additional catheter through the coronary sinus to stimulate the right ventricle (RV) and left ventricle (LV) in a coordinated fashion (Biventricular Pacing BVP, also called cardiac resynchronization therapy or CRT). BVP has been linked mostly to patients with Heart Failure and IEA. Due to the high expense, complexity and risk of BVP, it has not been widely utilized to prevent the IEA that is created by RV apex pacing in pacemaker patients that are not otherwise indicated for BVP. Thus, the second line of research, which has remained focused on the simpler approach of stimulating the interventricular septum, tries to achieve a more normal activation of the heart and, targets both patients with narrow and wide QRS complex that are indicated for a regular single or dual chamber pacemaker implant.

There are four types of pacemakers: (1) asynchronous; (2) single-chamber synchronous; (3) double-chamber AV sequential; and (4) programmable. Asynchronous (AOO, VOO, DOO) pacemakers discharge at a preset rate that is independent of a patient's (inherent) heart rate. Single-chamber synchronous (AAI, VVI) pacemakers discharge at a preset rate only when a patient's (spontaneous) heart rate drops below the preset rate. Dual-chamber AV sequential pacing (VDD, DVI, DDD) pacemakers usually use two electrodes: one in the atrial appendage and one in the right ventricular apex. The atrium is stimulated to contract first, then after an adjustable AV atrio-ventricular (AV) interval, the ventricle is stimulated. Programmable pacemakers have programmable features such as pacing rate, pulse duration, voltage output, and R-wave sensitivity, atrial tachycardia management features, atrial and sometimes ventricular anti-tachycardia pacing features, (programmable AV delays, dynamic AV delays, pulse width, automatic lead mode switching, etc.)

All of these types of pacemakers can be fitted with high voltage output and/or especial waveforms, like those discussed by U.S. Pat. Nos. 7,512,440; 8,005,544; 8,014,861; and 8,050,756; and U.S. Patent Publication No. 2012/0101539, in the right ventricular channel to restore a normal activation sequence by bypassing the conduction system block by pacing in the His bundle, in the right ventricular (RV) septum either in its right ventricular or right atrial portions. For simplicity we will call this type of high voltage/especial waveform His bundle therapy XSTIM in the rest of this disclosure.

Resynchronization therapy (CRT) and XSTIM aim to improve the heart's IEA by correcting this problem so as to improve cardiac function. Most of the information used to understand the benefits of CRT and XSTIM has been derived either from acute measurements of arterial pressures, and the rate of change of intraventricular pressures, or from outcome trials that assessed the mortality and hospitalization rate that the application of this therapy had on heart failure (HF) patients. Outcomes information, even though critical to understanding the actual clinical benefit of a therapy has not provided any information about the actual success of CRT in correcting the underlying problem for a given patient, it only provides the likely outcome for a population of patients. Hemodynamic information, although accurate in measuring the mechanical effects of CRT and XSTIM when they attempt to correct the underlying electrical asynchrony problem, is only a surrogate variable, since it does not provide corroborative information about the effectiveness of CRT or XSTIM in correcting the electrical asynchrony, currently thought to be the core problem creating the asynchrony. Furthermore, previous indications for the application of CRT do not require the prescribing physician to verify that the patient actually has mechanical asynchrony to start with. Because of this, aspects of the present disclosure emphasize the diagnostic evaluation of IEA and its optimization, both initially and post-implant, by an electrical method, through the parameters derived from electrical activity of the heart that is more accurate than the simple QRS width measurement required to determine the presence of LBBB, as is currently required by CRT's present clinical indication (http://www.theheart.org/article/1122825.do).

Prior to the implantation of a CRT device or a right ventricular pacing device, some patients have left bundle branch block (LBBB), a requirement for CRT's indication but not for right ventricular pacing. In general, the LBBB is accompanied by electrical and mechanical asynchrony, but its extent is not measurable with the surface ECG. Therefore, at this stage, previously developed techniques do not provide the prescribing physician or the implanting physician with any method to determine if the patient actually has asynchrony that could be corrected by implanting a CRT device. Additionally, previously developed techniques do not provide the implanting physician with any simple technique to determine whether the site chosen for stimulation is either correcting the electrical and mechanical asynchrony, as should be the case after a CRT implant, or not creating electrical and mechanical asynchrony during pacing after the implantation of a right ventricula, and/or a CRT pacing device. The asynchrony level could be worse during pacing than at the previous baseline in the particular patient under consideration for the implant site and/or sites chosen and/or available for fixating the lead and/or leads. For instance, all the studies done to prove the benefits of CRT are population based studies where most benefited but some did not. Further, previously developed techniques do not provide the implanting physician with any simple method to evaluate the optimum (from a reduction or avoidance of asynchrony point of view) atrio-ventricular (AV) delay or interventricular (VV) delay. Similarly, after the implantation, previously developed techniques do not provide the follow-up physician any simple method to confirm that the implanted CRT device is working correctly and is correcting the baseline asynchrony that caused the prescription of the device in the first place.

Previously developed techniques only allow the follow-up physician to know that the biventricular pacing (BVP) device is pacing in both chambers and capturing in both, but not whether or not the underlying IEA that caused the prescription of the BVP device has been corrected by the device. The only method available to the follow-up physician is to assess the degree of success through the visualization or narrowing of the QRS with a conventional ECG. This method, however, does not provide enough information to know if the left ventricle (LV) is asynchronous, or not, especially when the narrowing of ECG QRS is not marked as it occurs in most cases of CRT.

In cases of patients with a narrow QRS in need of a pacemaker, pacing will most likely widen the QRS, since any artificial stimulation will be worse than normal conduction, unless a method like XSTIM is used. However, this should be checked in order to determine the best implant site in the right ventricle such that the artificial stimulation created by pacing can be verified to either not worsen the intraventricular synchrony that existed before the pacemaker implant or to produce a therapeutically tolerable level of asynchrony, for the particular patient under treatment. Currently no such check is done and the right ventricular pacing lead is placed in the right ventricle without checking for the effect of pacing site on IEA in most centers. The reason IEA is not checked is that there are no simple easy to use, quick and inexpensive methods that allow for its evaluation.

Finally, after implantation, each patient needs specific programming adjustments, both at discharge and follow-up appointments to maintain the optimum level of asynchrony as his/her heart substrate is changing in adaptation to the new modality of electrical activation created by the stimulation therapy or to changes in the patient's drug regimen. Aspects of the present disclosure solve the aforementioned issues by providing the prescribing physician a simple non-invasive method to confirm the existence of asynchrony before recommending the implant of a CRT or XSYNC device, by allowing the implanting physician to select the optimum pacing sites that provide a therapeutically acceptable level of electrical asynchrony, and by allowing the discharge physician to program an initial atrio-ventricular and interventricular delay that ensure that the level of asynchrony is below the therapeutic target for the patient being treated. Additionally, aspects of the present disclosure solve the aforementioned issues by providing simple means to the referring physician to confirm that the electrical asynchrony that created the need for the referral for a CRT device has been improved by the device to his/her therapeutic target, and by also providing the standard pacemaker implanting physician the means to select a pacing site in the right ventricle that does not worsen electrical asynchrony above the therapeutic target he or she has after a regular right ventricular pacemaker is implanted. Further, aspects of the present disclosure utilize the intracardiac electrodes used for cardiac stimulation and/or the can of the stimulation device and/or any indifferent electrodes it may have to derive a pseudo-surface electrocardiogram (ECG) to be used as input data to evaluate the level of IEA. This type of ECG has the added advantage that allows the stimulation device to continuously change the atrio-ventricular delay and the interventricular delay (every second, every minute, every hours or as the follow up physician programs into the device) to optimize the pacing parameters to maintain asynchrony below the therapeutic target. To accomplish these goals, aspects of the present disclosure utilize either the surface ECG signals (or a pseudo ECG, derived from intracardiac signals) to compute an Intraventricular Electrical Asynchrony Index (IEAI).

Previously developed methods utilize several processes for evaluating the electro-mechanical asynchrony, one of them is ultrasound echocardiography. Within the ultrasound group, tissue Doppler Imaging (TDI) is the most common method used for measuring asynchrony. Ultrasound methods are highly inaccurate and imprecise due to the twisting motion of the heart wall during contraction (which only complex set ups account for, since different layers of tissue will move at different times, making the interpretation of asynchrony measurements very difficult). They are very expensive and time consuming and out of the realm of what the referring, follow-up and implanting physicians can have reasonable access to. Lack of knowledge and understanding of this factors has led to the proliferation of inaccurate methods for assessing asynchrony based on echocardiography and Doppler Tissue imaging with the consequence that none has been adopted as a clinical standard, leaving the implanting and follow up physician without a tool to use in the assessment of whether the therapeutic level of asynchrony prescribed has been reached or not. Furthermore, if during the implantation of a device the presence of echocardiographic recording systems is added, complexity is also added to the procedure, which increases the surgical time and thereby increases the cost of the procedure and the risk of infection. The time it takes to perform a relatively accurate ultrasonic evaluation of a single set of parameters on their impact in asynchrony levels is in the order of minutes. Aspects of the present disclosure would decrease that time to the order of seconds. Finally, given that the root cause of the degradation that is being corrected is the electrical conduction system of the heart, direct measurements of the effect of the therapy on that conduction is the best strategy for determining the success of the therapy, and not the measurement of secondary surrogate mechanical variables that them, themselves are very prone to measurement errors and miss-interpretation of their meaning.

Aspects of present invention will provide significant cost savings to the Health Care system that adopts them, since currently outcome based methods used to determine success of this therapy actually implant people that may not receive any benefit, but just belong to a statistically derived population or group or subset of the universe of patients that have a high likelihood of deriving benefit from the therapy when the lead position is not optimized. Furthermore, it is perfectly conceivable that subgroups inside the previously referred to subgroup could be worsened by the therapy since electrical stimulation could either be worsening electrical asynchrony in those who despite showing LBBB didn't have significant IEA or those whose lead position is such that it ends up worsening IEA from its baseline level. At the same time the present invention will provide significant benefit to society by enabling physicians to only treat those who need to be treated, and by providing inexpensive easy to use and quick tools for physicians to make sure that they are not only improving those patients whom they implant but that they are delivering no harm to any of them, including the patients that require pacing for reasons other than IEA and in whom the correction of their problem, requiring ventricular pacing, could be inadvertently triggering IEA and either increasing their probability of developing heart failure or if they already had it, accelerating its progression.

The above discussion is not intended to describe each embodiment or every implementation. The figures and following description also exemplify various embodiments.

BRIEF DESCRIPTION OF THE FIGURES

Various example embodiments may be more completely understood in consideration of the following detailed description in connection with the accompanying drawings, in which.

Figure 1:
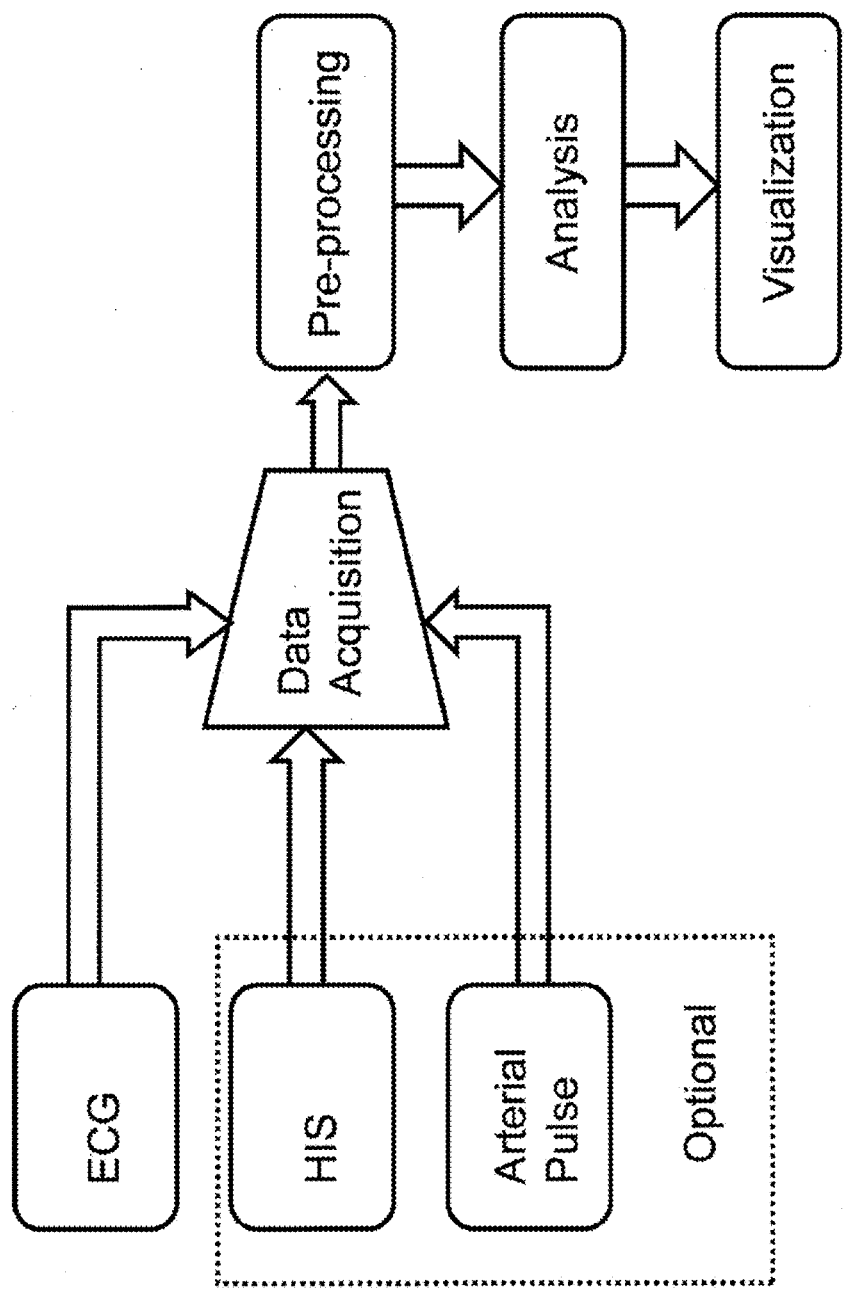
FIG. 1 shows an example block diagram of the acquisition system of signals (His and arterial pulse are optional), consistent with various aspects of the present disclosure.

While the disclosure is amenable to various modifications and alternative forms, examples thereof have been shown by way of example in the drawings and will be described in detail. It should be understood, however, that the intention is not to limit the disclosure to the particular embodiments shown and/or described. On the contrary, the intention is to cover all modifications, equivalents, and alternatives falling within the spirit and scope of the disclosure. In particular, aspects of the present disclosure refer to the minimum set of electrocardiographic leads that allow the simplest and most consistent asynchrony index (IEAI) calculation, but it should be obvious to those skilled in the art that other standard or non-standard lead combinations could be used in the derivation of the asynchrony index (IEAI).

DETAILED DESCRIPTION

Aspects of the present disclosure are directed toward a device that operates on the surface electrocardiogram (ECG) or on a pseudo-ECG derived from intracardiac electrodes, and/or leads, and/or any indifferent electrodes from the stimulation device to determine electrical asynchrony. Currently, one of the only ways to noninvasively measure mechanical asynchrony of the heart is through Tissue Doppler Imaging (TDI). The use of this technique implies considerable investment of capital resources, the incorporation of an echocardiographist in the operating room and an unacceptable (from the point of view of risk of infection, procedure length, operating room (OR), electrophysiology (EP) catheter time, implanting staff time) lengthening of the procedure time with the associated increase in cost and complexity. Furthermore, the twisting of the cardiac fibers during heart contraction makes this measurement extremely challenging, thus requiring very highly skilled operators in charge of the imaging and analysis of the data sets. Thus, the determination of asynchrony by various aspects of the present disclosure, simplifies the procedure in terms of staff (the same technician can make the connections and measurements), patient safety, cost, time and equipment.

Mathematically, the heart can be modeled as a large oscillator. Attempting a more realistic approach, one could say that the right heart and left heart are two oscillators with the same fundamental frequency and a time lag between them. More specifically, the left heart can be segmented into several coupled oscillators which according to their location will have different time delays or offsets between them still sharing the same fundamental frequency. Thus, the determination of asynchrony is subject to the measurement of this delay between oscillators in order to place the delay in a range of normality. Therefore, various aspects of the present disclosure utilize cross correlation between the signals of two, three, four and up to 8 leads of the surface ECG to determine phase differences between leads (this is because only 8 are linearly independent). Many combinations are possible and can provide results; after careful analysis in multiple patients of the advantages and disadvantages of the different combinations, we have determined that the simple approach of using only two leads allows us to obtain most of the required information without the extra complexity and cost of a more complex setting. For instance, aspects of the present disclosure are directed towards an ECG lead with inferior frontal view and one involving a lateral view. According to the dipolar theory, the leads are projections of the 3D instantaneous electrical vector of the heart onto two different planes; the horizontal and the frontal planes. On each plane, the leads account for the electrical vector projections in different directions, defined by the electrode location. These projections show anatomical correlations with specific regions or segments of the heart. Thus, lead II can provide information related to the inferior front side, and V5 or V6 can provide data on the side wall of the left ventricle. Therefore, it should not be surprising that this set of leads provided the best results in an exhaustive testing in patients of different lead combinations. Nevertheless, other lead combinations can produce similar results. As a result, aspects of the present disclosure can utilize several of various combinations of leads. For particular patients, the invention allows the physician to use his/her discretion to choose other pairs of leads to track a particular spatial distribution of asynchrony. For instance a simple approach would be to select the earliest and latest onset QRS complexes from the 8 linearly independent leads of the ECG (I, II, V1 to V6). Other approaches will become obvious to those skilled in the art after reading this disclosure, for instance using non standard ECG lead configurations, such as vectocardiography configurations. In another embodiment, all 12 leads are fed into the system and the system automatically detects the best set to use for the MAI calculations, using cross-correlation analysis between them and finding the set that best represents the spatial distribution of the dispersion of the activation wave-front. For simplicity in this disclosure we have only included the analysis and examples derived from the same pair of standard leads (lead II and V6). This approach has the added advantage of enabling the classification of the hundreds of patients we have studied into a limited set of asynchrony types (or curve types, FIG. 16).

FIG. 1 shows an example simplified diagram of system blocks, consistent with various aspects of the present disclosure. The first blocks of FIG. 1 represent ECG, His and arterial pulse signal measurement, and then acquisition of those signals in the second block. The third block shows pre-processing (e.g., digitization) of the signals in preparation for analysis, which is shown in the fourth block. After the signals are analyzed, the results are visualized, as shown in the fifth block.

In certain embodiments, an acquisition block (e.g., acquisition circuitry), consistent with various aspects of the present disclosure, includes filtering, conditioning and standard acquisition for signals. The signals are fed to the preprocessing block (e.g., preprocessing circuitry), which performs the detection and averaging of QRS complexes. Preprocessing operates on both user-selected leads and consists of the QRS complex detection using an algorithm based on Hilbert transform, the sampling of these complexes on a window of typically 150 ms backward and 120 ms forward, their alignment and subsequent averaging.

Figure 2:
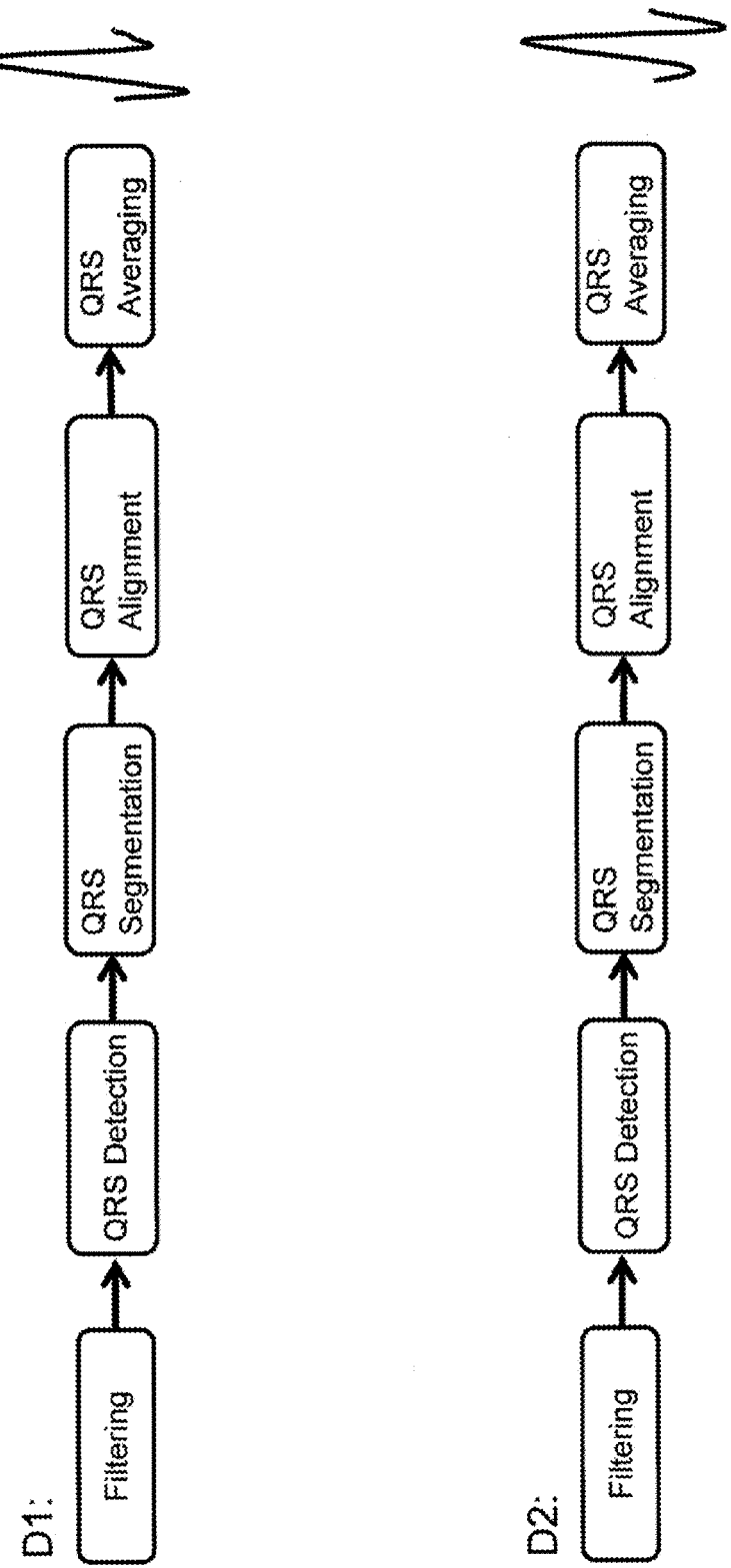
FIG. 2 shows an example block diagram of electrocardiogram signal preprocessing, consistent with various aspects of the present disclosure.

FIG. 2 shows an example schematic of signal preprocessing flow. FIG. 2 shows that QRS complexes from both leads are first fed to a filtering block, then to a detection block, after that they are both fed to a segmentation block, after that they are both aligned in the QRS alignment block and ensemble averaged in the last block with at least 4 beats. During the online analysis, the ensemble average was done using an exponential ensemble averaging approach and during the offline analysis the beats selected by the operator were ensemble averaged.

Figure 3:
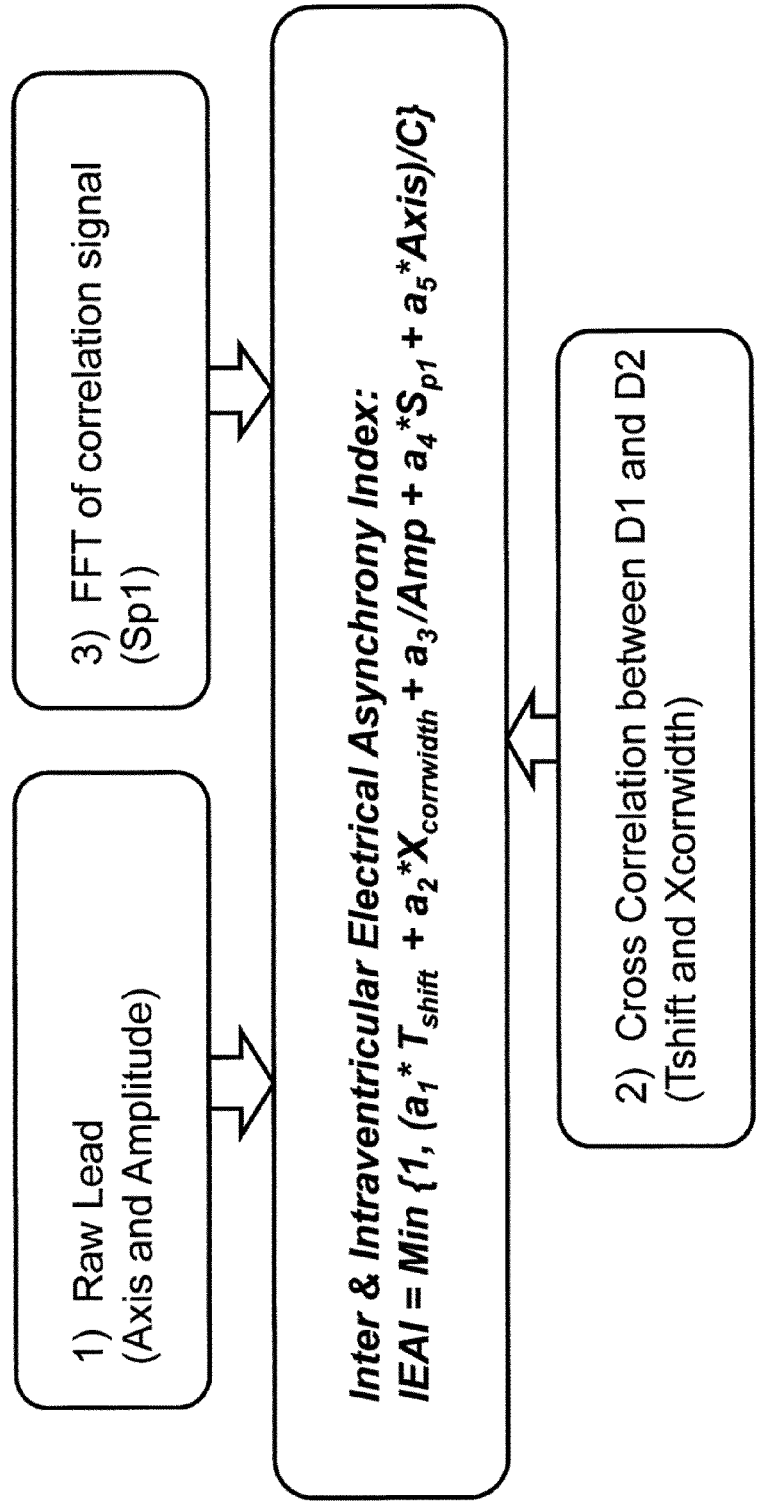
FIG. 3 shows an example block diagram of an analysis block, consistent with various aspects of the present disclosure.

FIG. 3 shows an example breakdown of an analysis block (e.g., analysis circuitry). In the first block, parameters are extracted from the incoming averaged QRS complexes from D1 and D2, Axis and Amplitude are obtained in block 1, cross-correlation of both leads is performed in block 2, and finally the power spectrum of the correlation signal is obtained through the Fourier transform (FFT) in block 3.

The complete equation for the calculation of the asynchrony index (IAEI) is as follows:

$$IAEI = \text{Min}\{1, (a_1 * \text{abs}(T_{shift}) + a_2 * X_{corrwidth} + a_3/\text{Amp} + a_4 * S_{p1} + a_5 * \text{Axis})/C\}$$

Where Amp is an average amplitude, calculated as the mean of the peak to peak amplitudes of the leads D1 and D2. Thus, $\text{Amp} = (D1_{pp} + D2_{pp})/2$, where $D1_{pp}$ and $D2_{pp}$ are the peak to peak amplitudes of D1 and D2. In other embodiments of the present invention Amp could be selected to be either the amplitude of D1 or of D2. The values of the IEAI mentioned in this disclosure were obtained with our prototype where the amplitude of D2 was selected as the source of Amp (Lead II or DII).

The calculation of the cross correlation shown in FIG. 4 was done as follows.

Let X be the cross-correlation signal between D1 and D2, both of length N:

$$X(n) = \sum_{\tau=0}^{2N} D1(\tau) * D2(n + \tau)$$

$T_{shift}$ is the delay between the two leads measured as the time of peak obtained from the cross-correlation signal of D1 and D2: $T_{shift} = \text{MaxArg}_n[X(n)]$. $X_{corrwidth}$ is the width of the measured correlation signal to 70% of the peak amplitude of the signal correlation. Let $X_{wl}$ and $X_{wr}$ be the first sample points at which $X(n) \leq 0.7 * \max[X(n)]$ to the left and to the right of $\max[X(n)]$ respectively. Then, $X_{corrwidth} = \text{Arg}[X_{wl}] - \text{Arg}[X_{wr}]$. An example measurement of the correlated signal parameters ($T_{shift}$ and $X_{corrwidth}$) are displayed in FIG. 4. In accordance with aspects of the present disclosure, $T_{shift}$ points to the time of the correlation peak and $X_{corrwidth}$ to its width (being measured at 30% amplitude of the peak amplitude).

The FFT of the correlation signal was calculated as follows.

Let S be the discrete frequency transform of X(n), with a frequency resolution of 0.293 Hz: $S(w) = \text{fft}(X(n), 4096)$.

$S_{p1}$ is a spectral power factor, computed as the ratio of the low frequency band with respect to the complete frequency band of S(w):

$$S_{p1} = \frac{\sum_{0}^{10} S(w)^2}{\sum_{0}^{40} S(w)^2}$$

Figure 4:
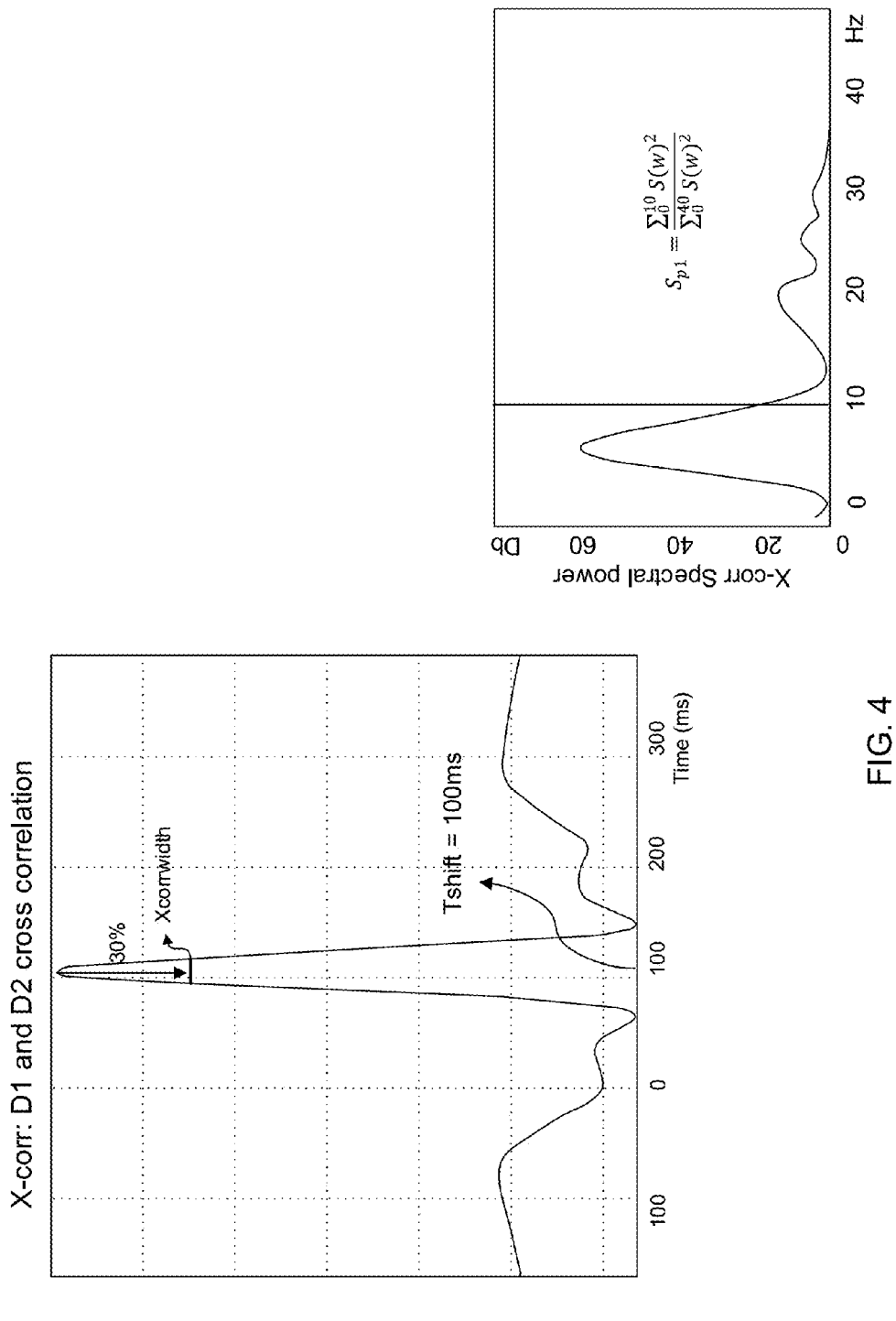
FIG. 4 shows an example actual calculation of parameters $T_{shift}$ and $X_{corrwidth}$ from the D1-D2 cross-correlation signal, and SP1, in accordance with various aspects of the present disclosure.

An example of the FFT of the correlation signal and the calculation of Sp1 is shown in the bottom right portion of FIG. 4. Further, Axis is a term related to QRS morphology. It can operate on the correlation signal, and can be calculated by the following algorithm, according to different combinations of polarity and amplitudes.

```
a=max([max(D1) abs(min(D1))]);
if (a/(min(D1)))==-1
    a=-a;
end
b=max([max(D2) abs(min(D2))]);
if (b/(min(D2)))==-1
    b=-b;
end
c=a*b;
Axis=0;
if c<0
    Axis=2
else
    if a<0
        Axis=4
    end
end
```

Figure 5B:
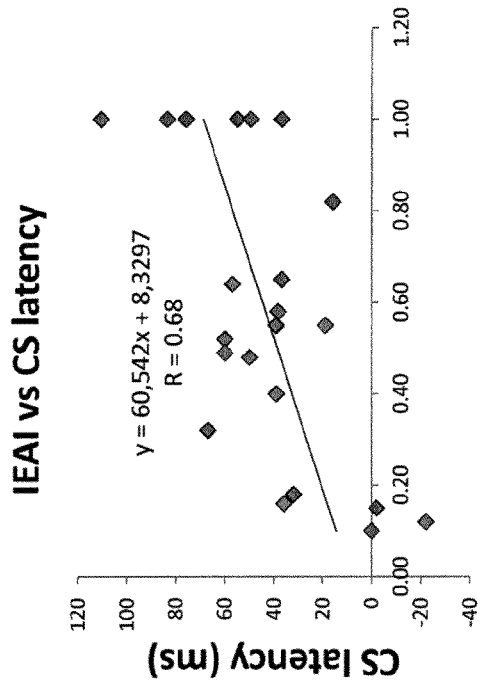
FIGS. 5A-5B show validation of various aspects of the asynchrony index (IEAI) as described in the present invention, versus a previously-developed technique by showing the correlation between Tissue Doppler Imaging (TDI) and Coronary Sinus latency (CS) versus the IEAI.

The $a_i$ values have been empirically fit so that IEAI presented maximal correlation with the activation latency recorded with a catheter on the most distal portion of the coronary sinus (CS in FIG. 5B). C is a scaling factor that affects all the terms equally, and $2 < C < 10$.

The numerical values of IEAI mentioned in this disclosure were obtained using the following set of values for $a_i$: $a_1 = 0.44$; $a_2 = 0.00$; $a_3 = 1$; $a_4 = 0.72$; $a_5 = 0.5$ and $C = 6$ for a sampling frequency of 1200 Hz per channel and a least significant bit; LSB=1.9531 uV relative to an input from the ECG. Min is the minimum function and returns the minimum value items separated by a colon between parentheses.

Example span for the coefficients $a_i$ are:

$a_1$: $0 \leq a_1 \leq 1$
$a_2$: $0 \leq a_2 \leq 1$
$a_3$: $1 \leq a_3 \leq 5$
$a_4$: $0 \leq a_4 \leq 1$
$a_5$: $0 \leq a_5 \leq 1$.

Figure 5A:
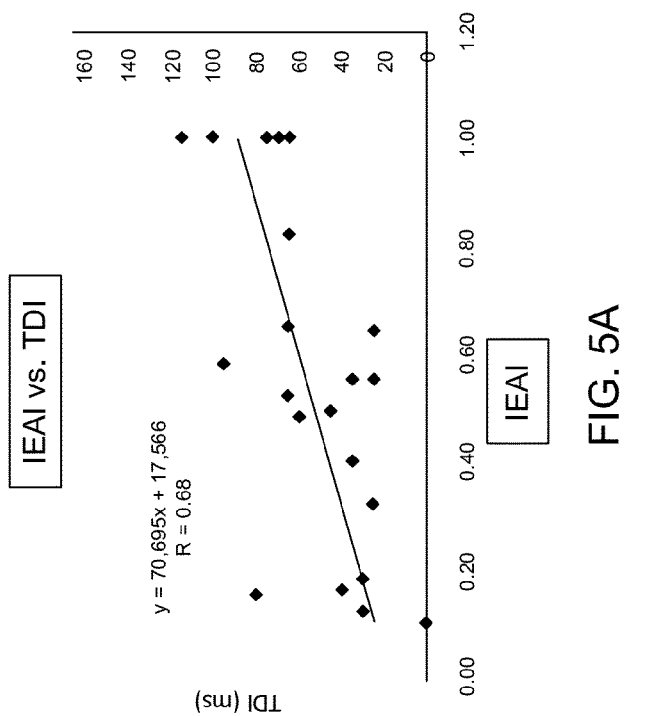

Certain aspects of the present disclosure are directed toward an asynchrony index (IEAI). The IEAI varies between 0 and 1, with increasing asynchrony values. A value close to 0 shows normal levels of synchrony while values close to 1 show a pathological asynchrony. Furthermore, we found that there is a correlation between asynchrony data measured with Tissue Doppler Imaging (TDI) and this index IEAI, thereby showing validation of various aspects of the present disclosure against previously utilized methods. The correlation between TDI and IEAI is shown in FIG. 5. Additionally, in accordance with various aspects of the present disclosure, an algorithm is utilized to automatically or manually measure the QRS duration either from the QRS complex directly or from the ensemble averaged QRS waveform (AAQRSC) to assist in pacing site location.

Figure 6A:
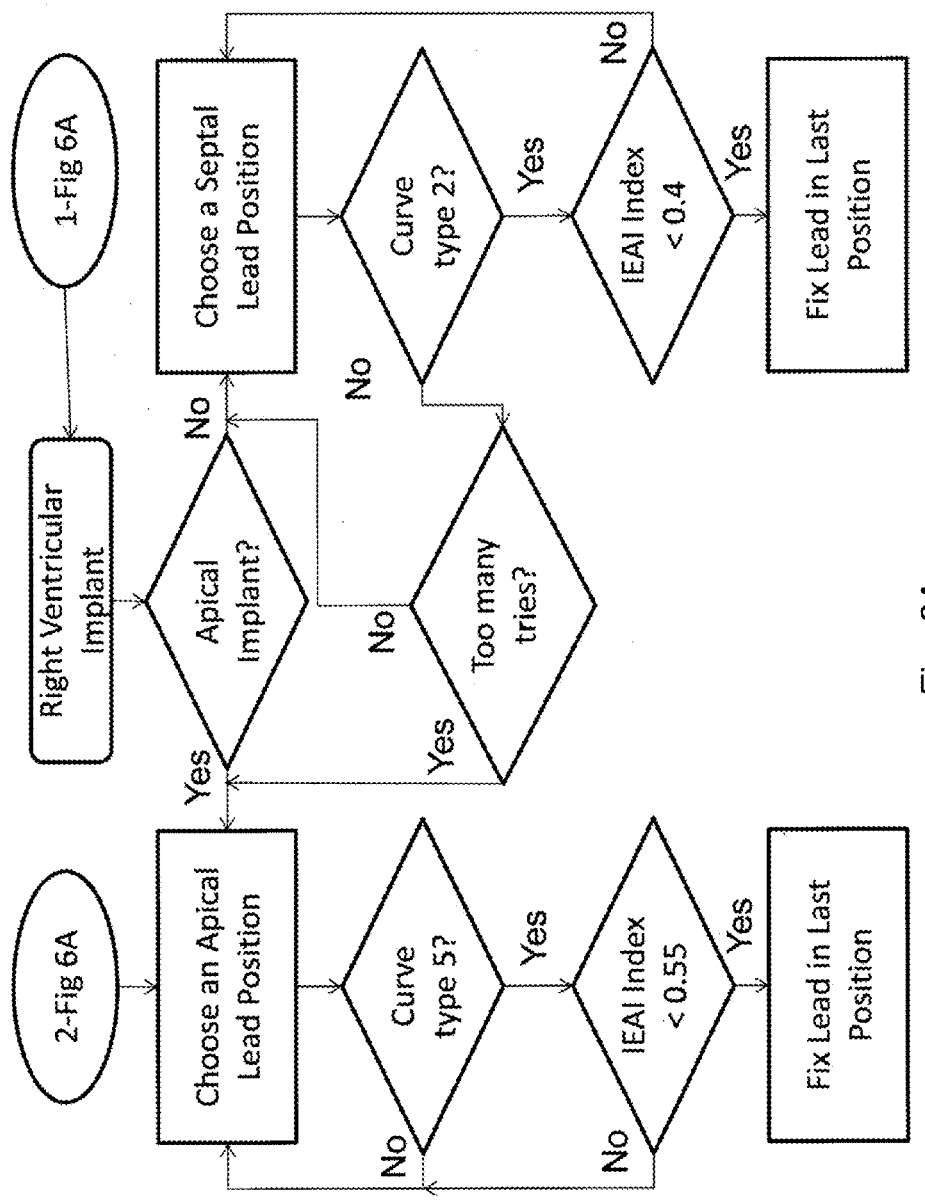
FIG. 6A shows a block diagram of an example workflow during a right ventricular (RV) pacing device implantation to help the implanters decide where to fix the right ventricular lead, utilizing various aspects of the present disclosure (the tries counter has been obviated for simplicity, in the apical lead position side (left))
Figure 6B:
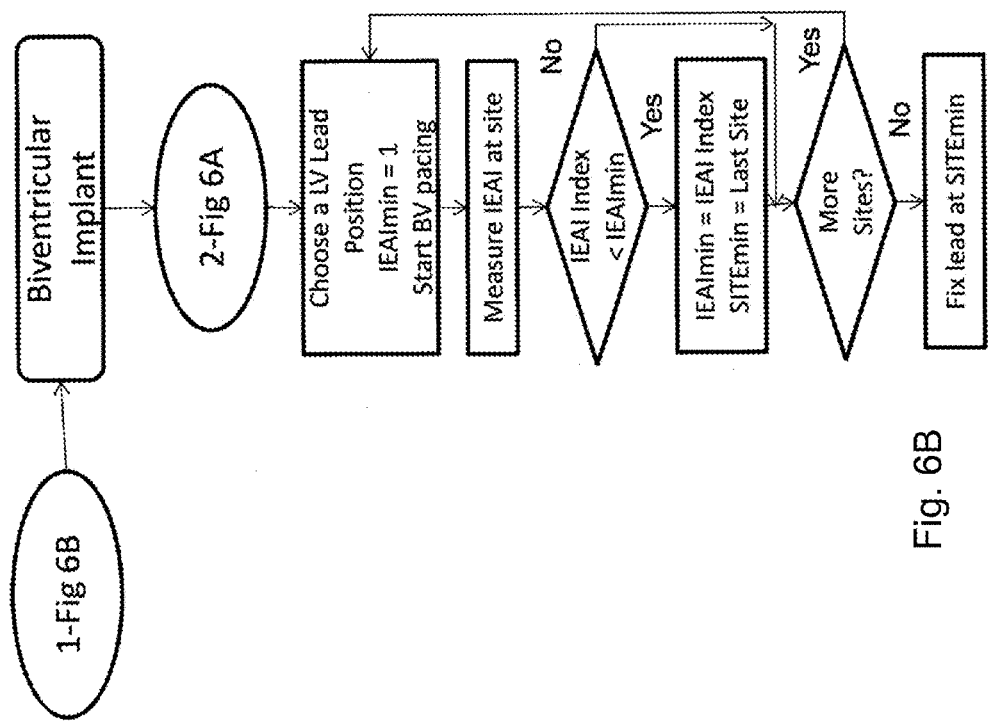
FIG. 6B shows a block diagram of an example workflow during a Biventricular pacing device implantation, utilizing various aspects of the present disclosure.
Figure 6C:
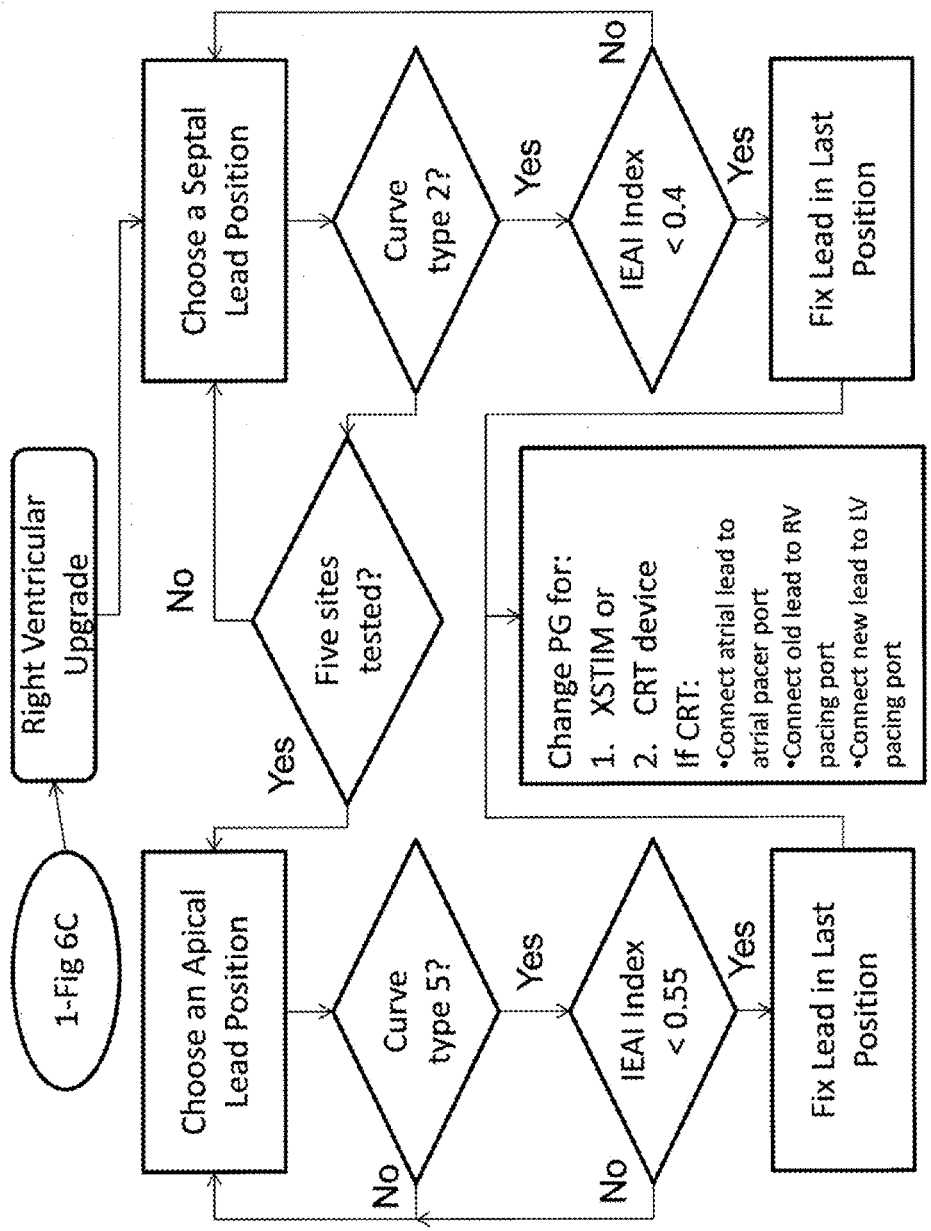
FIG. 6C shows a block diagram of an example workflow (sites tested counter obviated for simplicity reasons in the apical lead position side (left)) during a right ventricular pacing upgrade device implantation, utilizing various aspects of the present disclosure.

The asynchrony index (IEAI) changes with the location of the pacing site or sites (whether it is about a pacemaker or a CRT device), provided that the different pacing sites (at the programmed VV delay) create differences in the underlying level of electromechanical asynchrony. In some patients, changing the location of the pacing site may not create measurable changes in the asynchrony index. For those cases we use the automatic/manual measurement of the QRS complex (or the AAQRSC) duration. This measurement has been included into our prototype system and used in our clinical studies, and has been implemented in various embodiments of the present disclosure. Thus, if no results come from the asynchrony index, a second variable in the narrowing of the QRS complex can be observed. The automatic measurement of the QRS width follows these main steps: 1) Bandpass filter at 5-15 Hz to enhance the QRS complex; 2) Locate the peak of the complex (maximum for R waves and minimum for Qs waves); 3)—Set the peak as a fixed reference and move forward and backwards to find the point with the maximum derivative in absolute value (it can be positive or negative); and 4). From that point on, go further until the derivative (the first difference) drops more than 30%. The visual output of this block is two calipers marking the onset and end of the QRS complex. Additionally, various embodiments of apparatuses of the present disclosure measure QRS duration (manually or automatically). The screen displays three different colors, namely: green for widths less than 100 msec, yellow for values between 100 and 120 msec, and red when they are longer than 120 msec. Further, in another embodiment and to avoid noise from affecting the measurement, the above mentioned measurements of the width of the QRS complex are performed on the AAQRSC rather than on the QRS complex itself. FIG. 6A shows a simplified flow diagram describing the implementation of one of the embodiments of the present disclosure. This simplified example flow diagram deals with the most common situation where the changes in lead position influence the IEAI. If that were not the case or if the physician has doubts between two or more sites with similar IEAI, the system guides the operator to use the QRS width as the decision variable for equal IEAI. In FIG. 6A a right ventricular implant is shown and further described below, consistent with the embodiments of the present disclosure. First the physician makes a decision between an apical or a septal implant based on clinical and technical aspects of the patient and the system to be implanted (for instance an XSTIM system would be implanted in the septum), in the case of a septal implant the lead is placed in a first site and the IEAI is obtained along with the curve type (see FIG. 16), if a curve type 2 is obtained and if the IEAI index is below 0.4, the physician can stop and implant at that site. Alternatively, the physician could keep on trying more sites to lower the index even more, depending on the therapeutic target desired with regards to the level of asynchrony acceptable to the particular patient. We have found that an IEAI value of 0.4 is a reasonable and achievable goal. If no site is found on the septum that can achieve this targets (curve type 2 and IEAI<0.4) after 5 sites are tested, the algorithm recommends the implanting physician to then test the apical sites to see if a curve type 5 with an IEAI<0.55 can be achieved. In our experience, it was possible to find a site in the septum with IEAI<0.4 in most cases, therefore if the implanter can't find an IEAI lower than 0.4, the safest alternative is to recommend that they switch to an apical implant. Once this set of tests is completed (we have not repeated for simplicity the 5 tries counter on the apical site, but it is not advisable to try more than 5 times due to time reasons), and if no site that meets the described criteria has been found, the physician needs to make a decision of the best site to implant the lead based on the relative level of asynchrony found in apical and septal sites tested according to the IEAI value measured at those sites and the therapeutic target required for the patient, if necessary a CRT or XSTIM system implant should be considered. FIG. 6B shows a simplified flow diagram for a biventricular (or CRT or CRTD) implant, it first sends the physician through the same procedure as for a right ventricular implant (FIG. 6A) and then asks to place the left ventricular lead in a first position and start BV pacing until the last possible site is explored and its IEAI determined. It recommends the lead to be fixed at the site with the lowest value of IEAI. FIG. 6C deals with a pacemaker upgrade and follows the same procedure as in FIG. 6A. We have neither included a site counter on the apical site of the diagram, but it should be apparent that one is required and again we recommend 5 sites or less. For best asynchrony results and to use the existing lead, this embodiment upgrades the existing pacemaker to a CRT or biventricular device (with or without defibrillator) and recommends connecting the old lead to the RV port of the CRT device and the new lead positioned according to this IEAI to the LV pacing port. This is especially useful for a complete AV block patient because it gives him a back up pacing site in case there is a threshold increase at the new septal pacing site. Alternatively an XSTIM device could be used to upgrade the existing pacemaker.

Figure 7A:
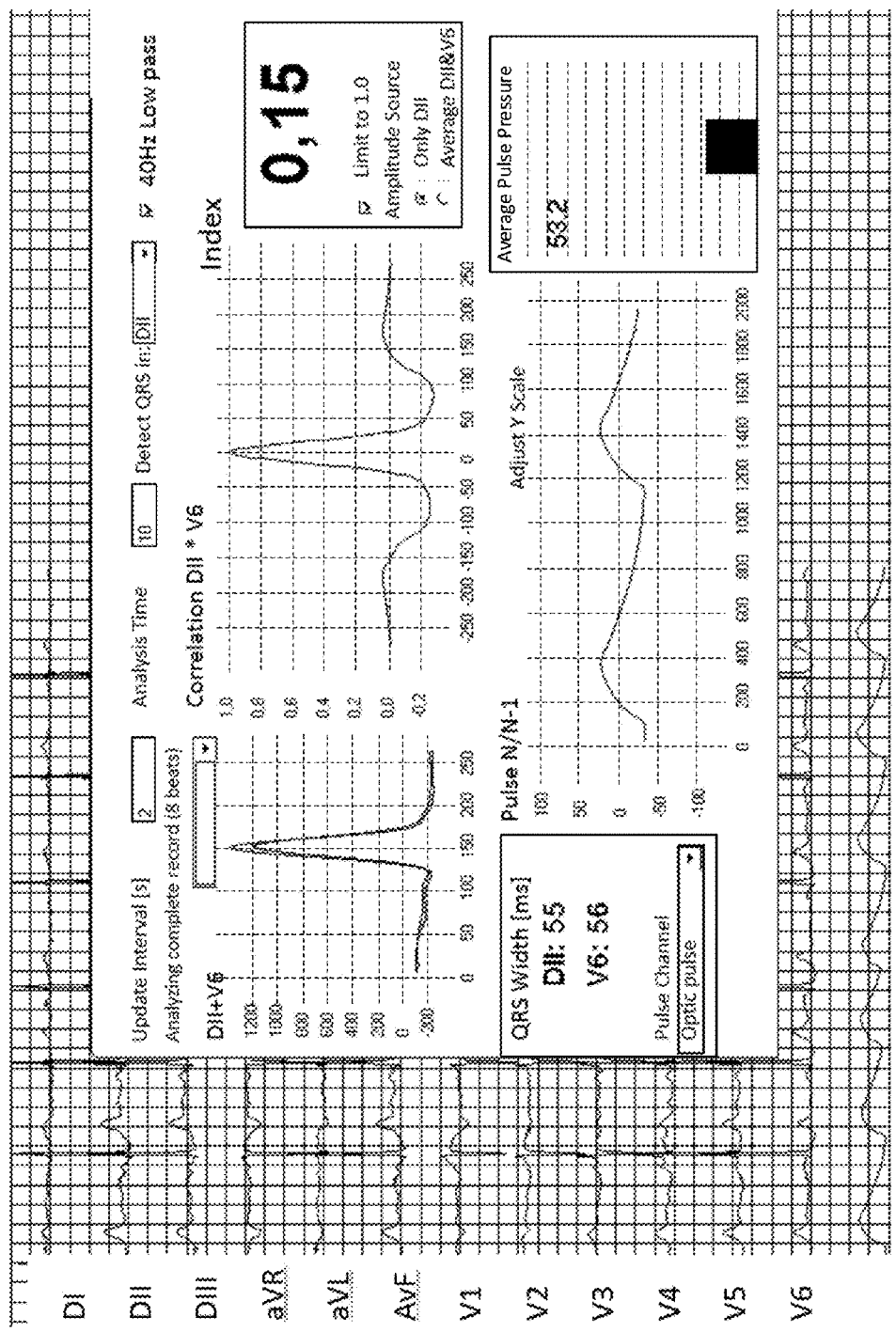
FIGS. 7A-7B show an example comparison of a baseline patient having asynchrony and LBBB (FIG. 7B) and a patient without asynchrony (FIG. 7A), consistent with various aspects of the present disclosure.
Figure 7B:
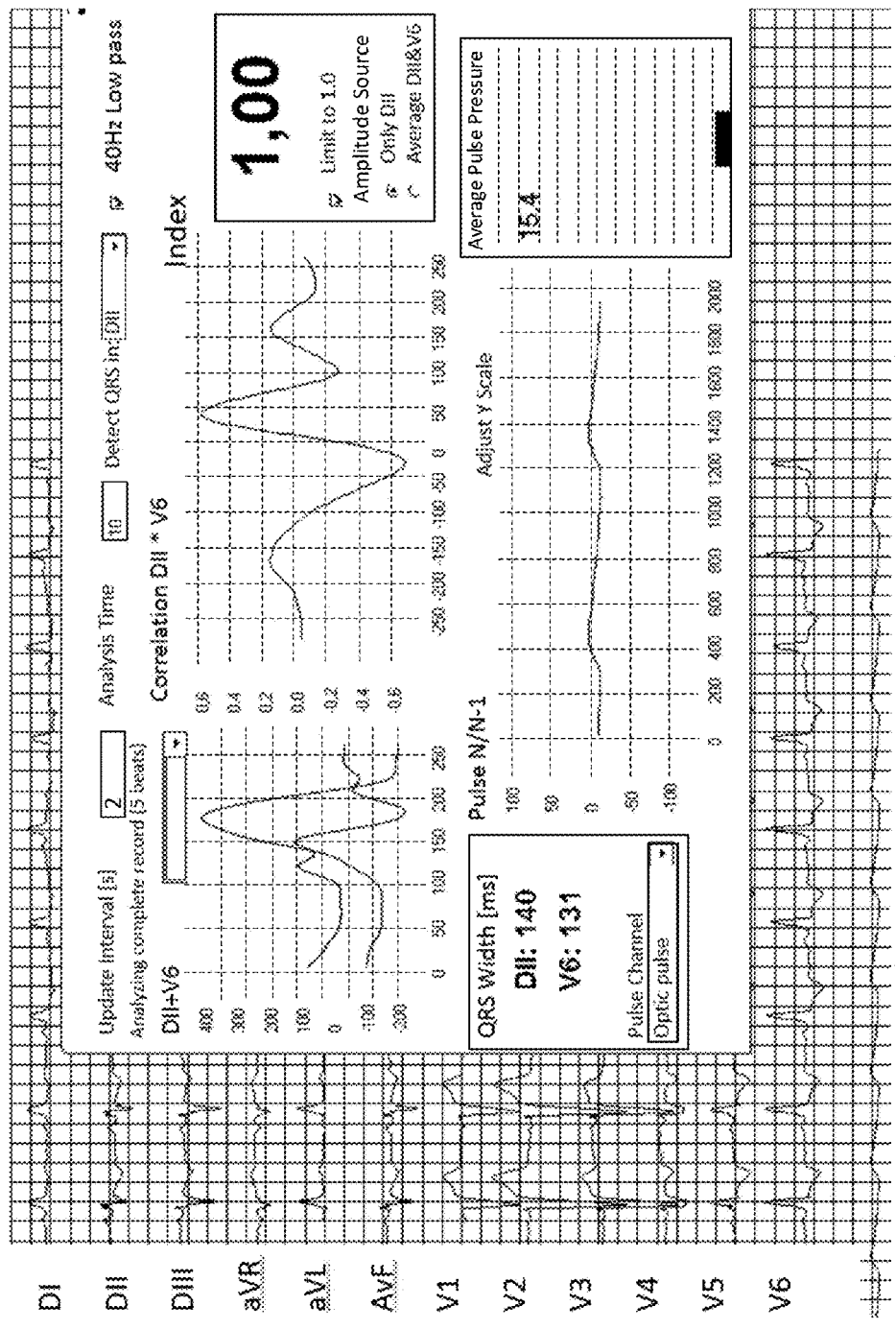

FIGS. 7A-7B show diagnostic results of application of an apparatus that is consistent with various aspects of the present disclosure. The first case presented is a normal subject with an electric intraventricular asynchrony index of 0.15 (FIG. 7A) versus a subject with a LBBB and an IEAI of 1 (FIG. 7B). The upper left panel of both FIG. 7A and FIG. 7B show the surface ECG, and the upper right panel of both FIG. 7A and FIG. 7B show averaged QRS complex. The left middle panel of both FIG. 7A and FIG. 7B show the resulting correlation, and the bottom left panels show the power and phase spectra obtained from the FFT signal correlation. Notice the gap between D1 and D2 in the case of the subject with LBBB compared to the healthy subject as well as the morphology of the correlation signal, which is wide and not centered in the patient with LBBB.

Figure 8A:
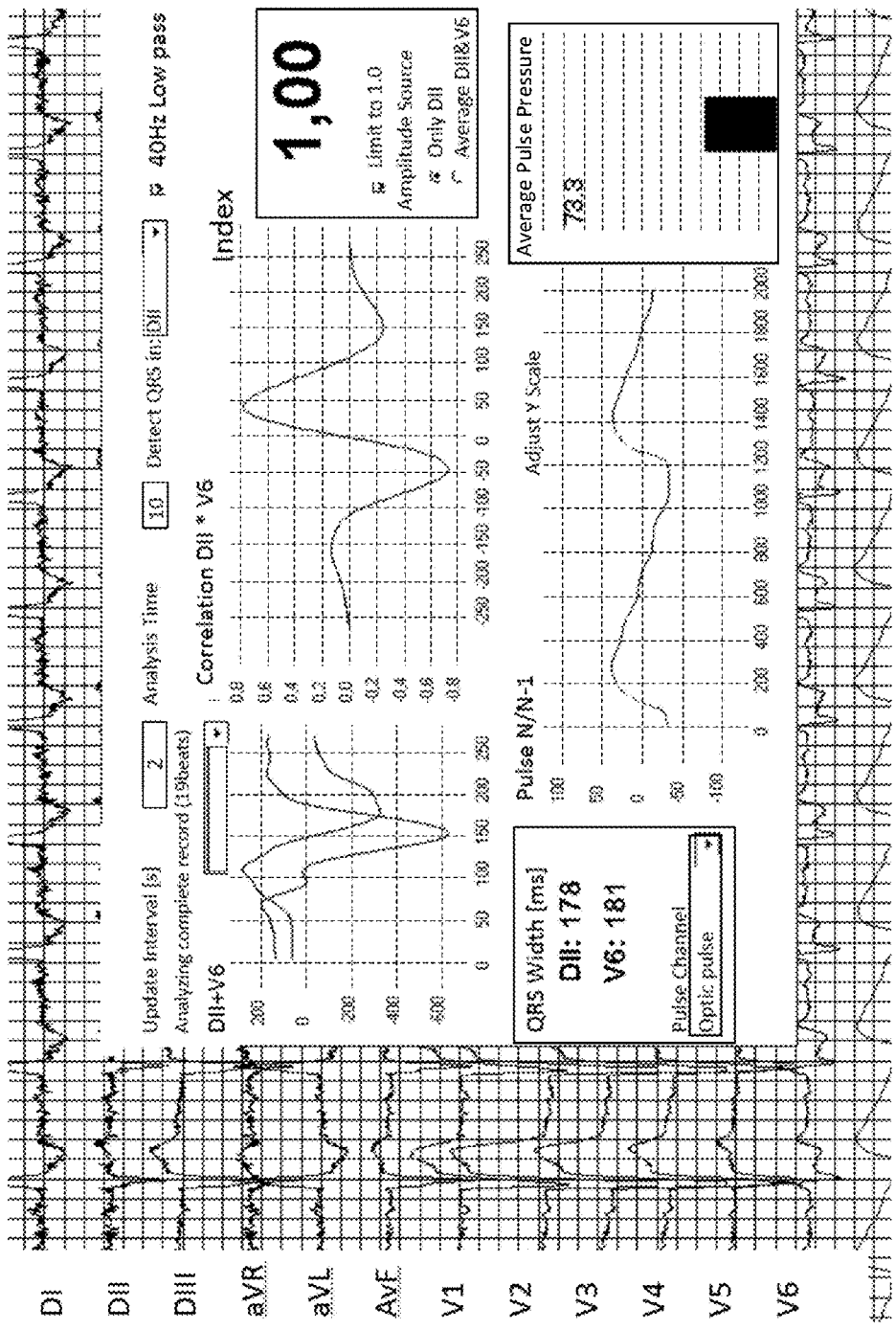
FIGS. 8A-8B show an example comparison between a patient with left bundle branch block (LBBB) without resynchronization (FIG. 8A) and with resynchronization (FIG. 8B)
Figure 8B:
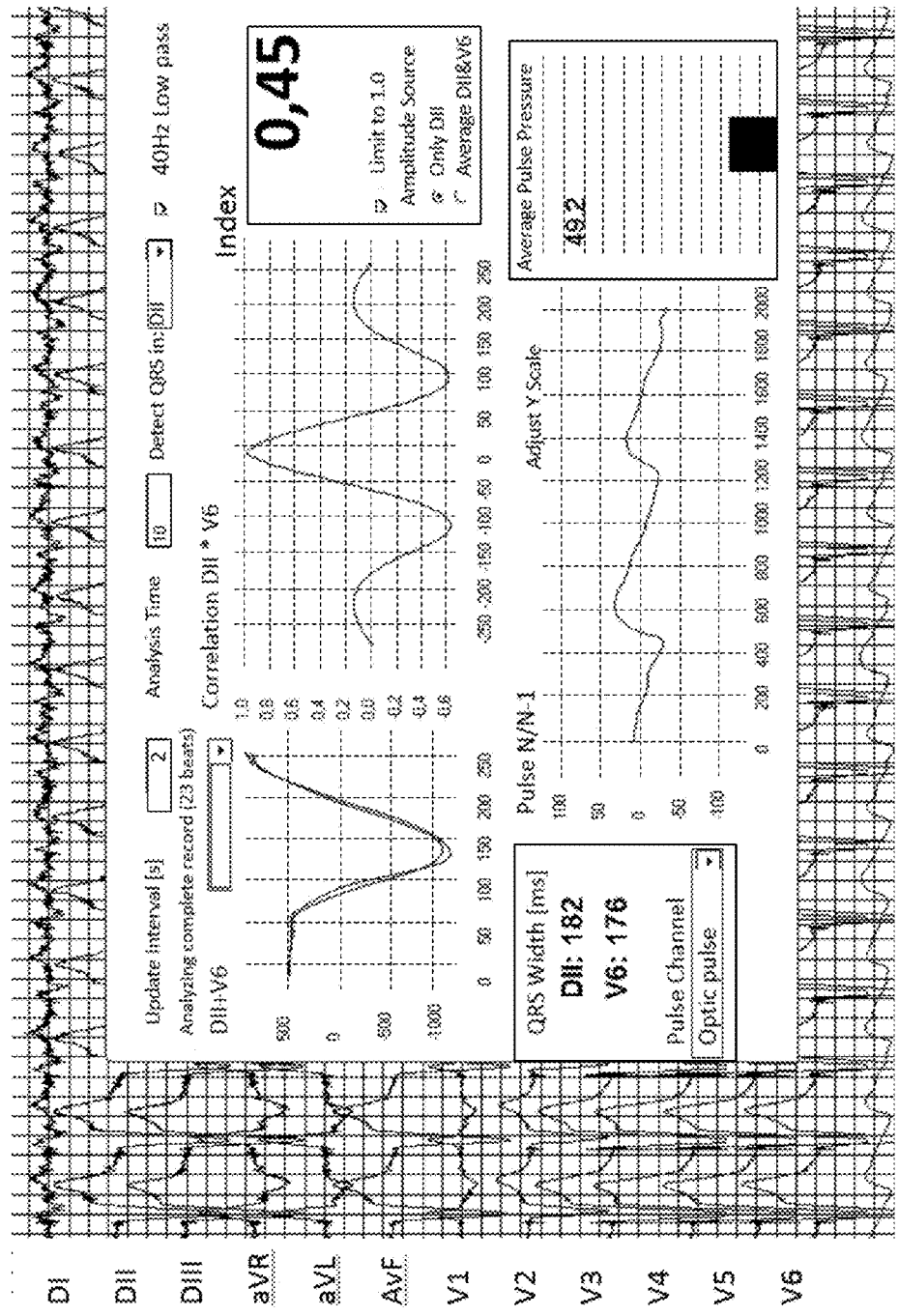

FIGS. 8A-8B show experimental results during the implant procedure of a resynchronization device, consistent with various aspects of the present disclosure, in a patient with LBBB. Note the difference between the baseline state of the patient, completely asynchronous, with an IEAI of 1 (FIG. 8A) and the status of the patient with resynchronization turned on, fully resynchronized with a IEAI of 0.45 (FIG. 8B). A change of axis can also be observed in the surface ECG, as well as the narrowing of the correlation signal and its centering around zero.

Figure 9A:
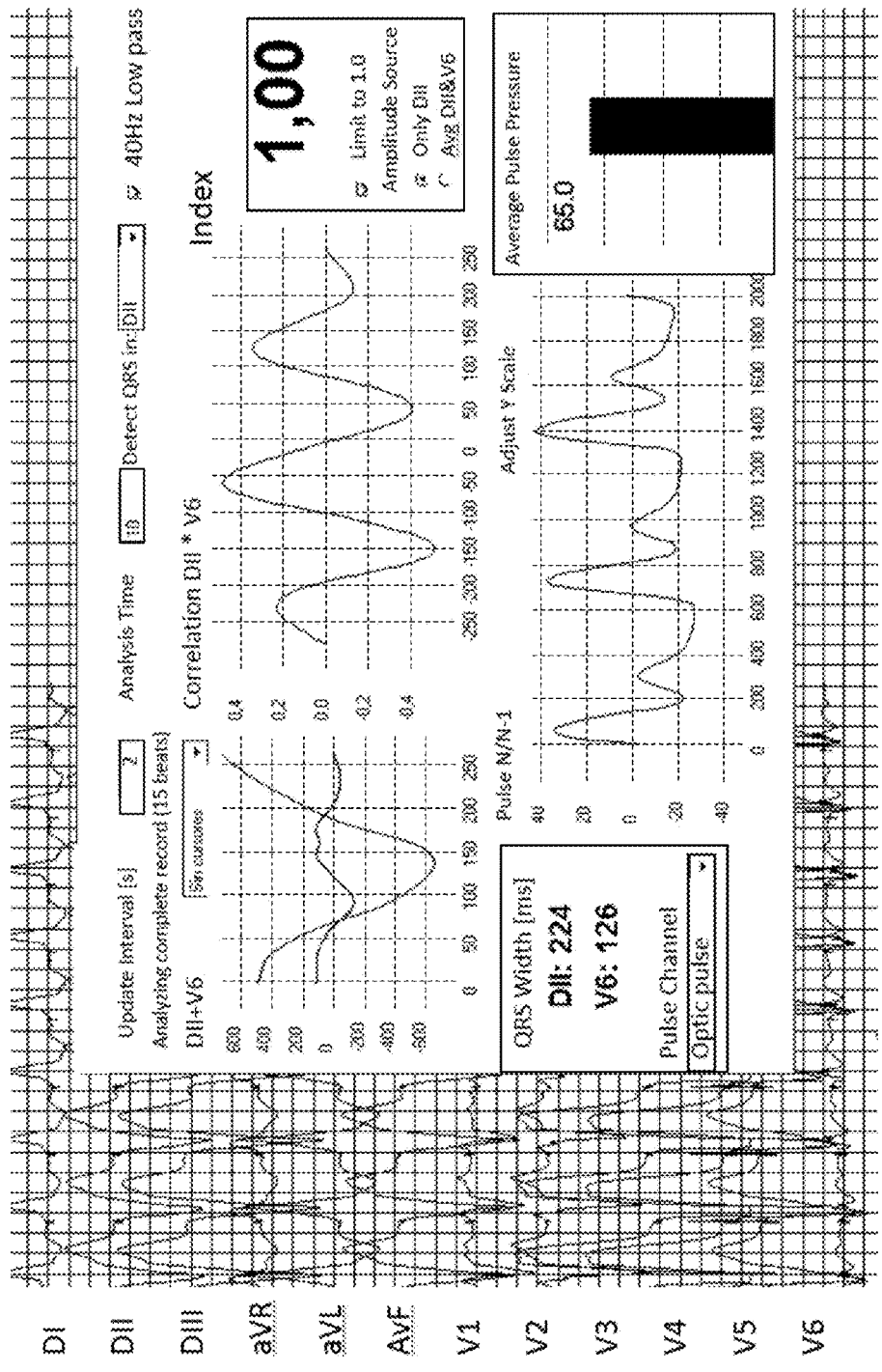
FIGS. 9A-9B show an example comparison between a patient with LBBB and implanted resynchronization device, consistent with aspects of the present disclosure, without capture in the left ventricle (FIG. 9A) and with capture the left ventricle (FIG. 9B)
Figure 9B:
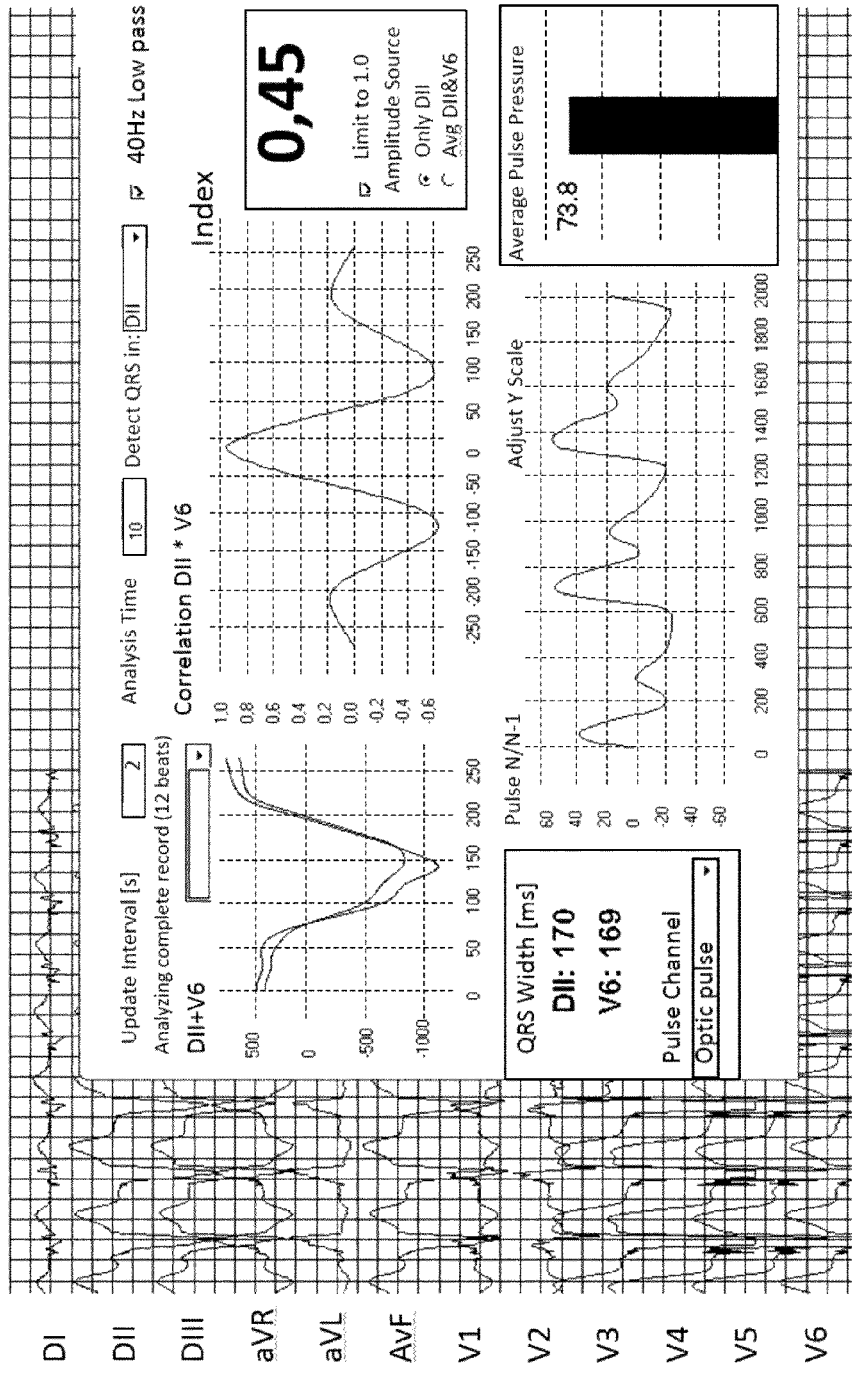
Figure 10:
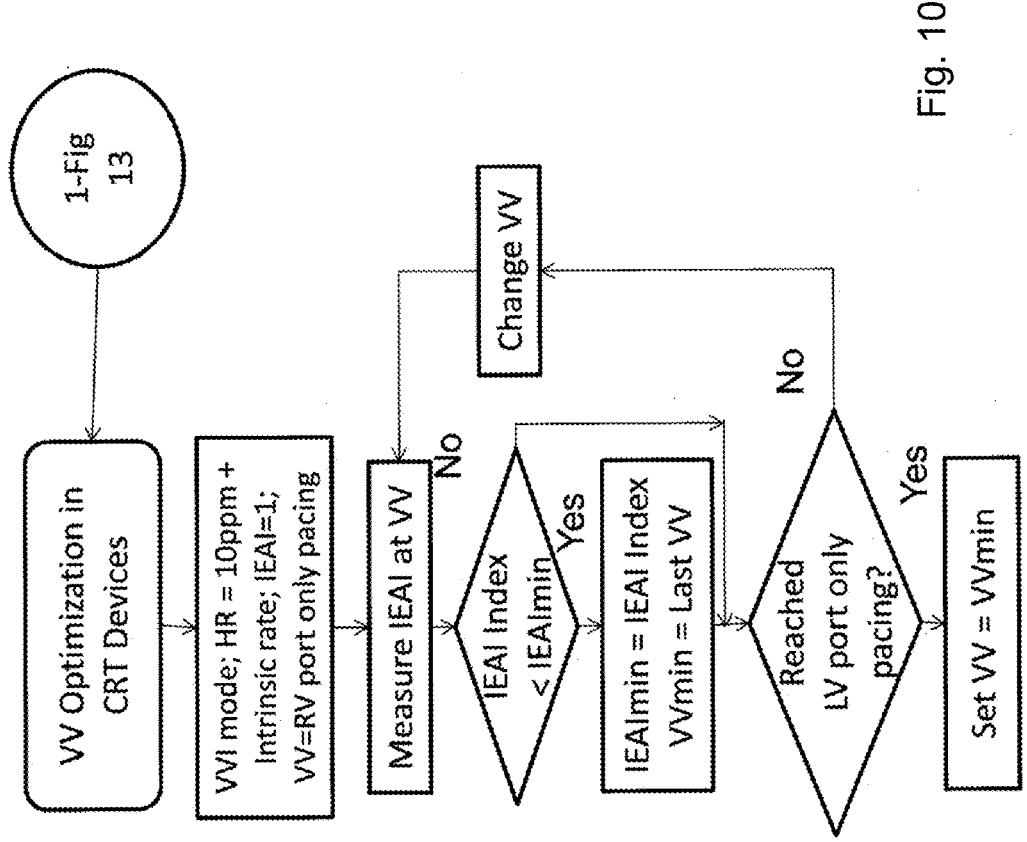
FIG. 10 shows an example flow diagram of VV interval optimization used in CRT (or Biventricular) devices, where the algorithm finds $VV_{min}$, meaning the VV interval that minimizes the asynchrony index IEAI, in accordance with various aspects of the present disclosure.

FIGS. 9A-9B show experimental results displaying the usefulness of an apparatus of the present disclosure for the follow-up of an implanted pacemaker. For instance, the LV pacing threshold can be higher than the programmed pacing amplitude. This situation of LV pacing without capture nullifies the desired resynchronization effect. As a result, the parameters of the resynchronization device can be changed, increasing the LV pacing output to achieve consistent capture. In FIG. 9A, the status of the LV is shown without capture for a patient with LBBB (IEAI=1) while FIG. 9B shows the same patient with this situation corrected by increasing LV pacing output (IEAI=0.45). Once the pacing site is determined by utilizing the asynchrony index, the index can be further used to determine VV delay. FIG. 10 shows a simplified flow diagram of the VV optimization performed by this invention on a biventricular or CRT pacing device. Basically, the optimum VV delay is the one that provides the minimum value of the asynchrony index while VVI pacing at a constant rate, usually 10 bpm above intrinsic rate. To obtain the optimum VV delay, the device is programmed to VVI pacing mode and both the right (RV) and left ventricular (LV) outputs are enabled and programmed above capture threshold. At that state, the VV space is scanned from RV only pacing all the way to LV only pacing passing through the simultaneous biventricular pacing (BV) when both outputs are sent at nearly the same time by the system (for instance separated by a zero to a few milliseconds). For each step in VV interval, the asynchrony index is measured and the optimum VV interval is chosen as the one that gives the minimum asynchrony index. In the case where more than one interval gives the same index, then the VV interval with the narrowest AAQRSC is chosen as the optimum interval. This method allows us to optimize ventricular synchrony independently of the value of the AV delay.

Additionally, in various embodiments, the information from the arterial pulse wave can be used to determine the optimum AV interval. Additionally, multiple embodiments of the present disclosure can utilize an online measurement of arterial blood pressure, which is useful for hemodynamic assessment of optimal AV interval programming in dual-chamber pacemakers. As a result of this measurement, AV interval optimization in regular standard cardiac pacing and in cardiac resynchronization therapy can be accomplished by varying the AV interval and simultaneously measuring the resulting arterial pulse pressure for a number of beats. Our prototype system allows the averaging of an operator defined number of beats to perform this measurement, and different embodiments use 8 to 64 beats for each AV delay. In still another embodiment, a full number of respiratory cycles is averaged to eliminate respiration as a source of variation of arterial pulse pressure. In still another embodiment the respiratory cycle is detected automatically by the system using the modulation it produces in the pulse rate and in the pulse amplitude, once the cycle is identified the system is automatically set to acquire ECG and pulse pressure data for 2 complete respiratory cycles for each AV delay tested. Aspects of the present disclosure are directed toward pulse signal improvement with different AV delays by optimizing left ventricular preload.

Figure 11A:
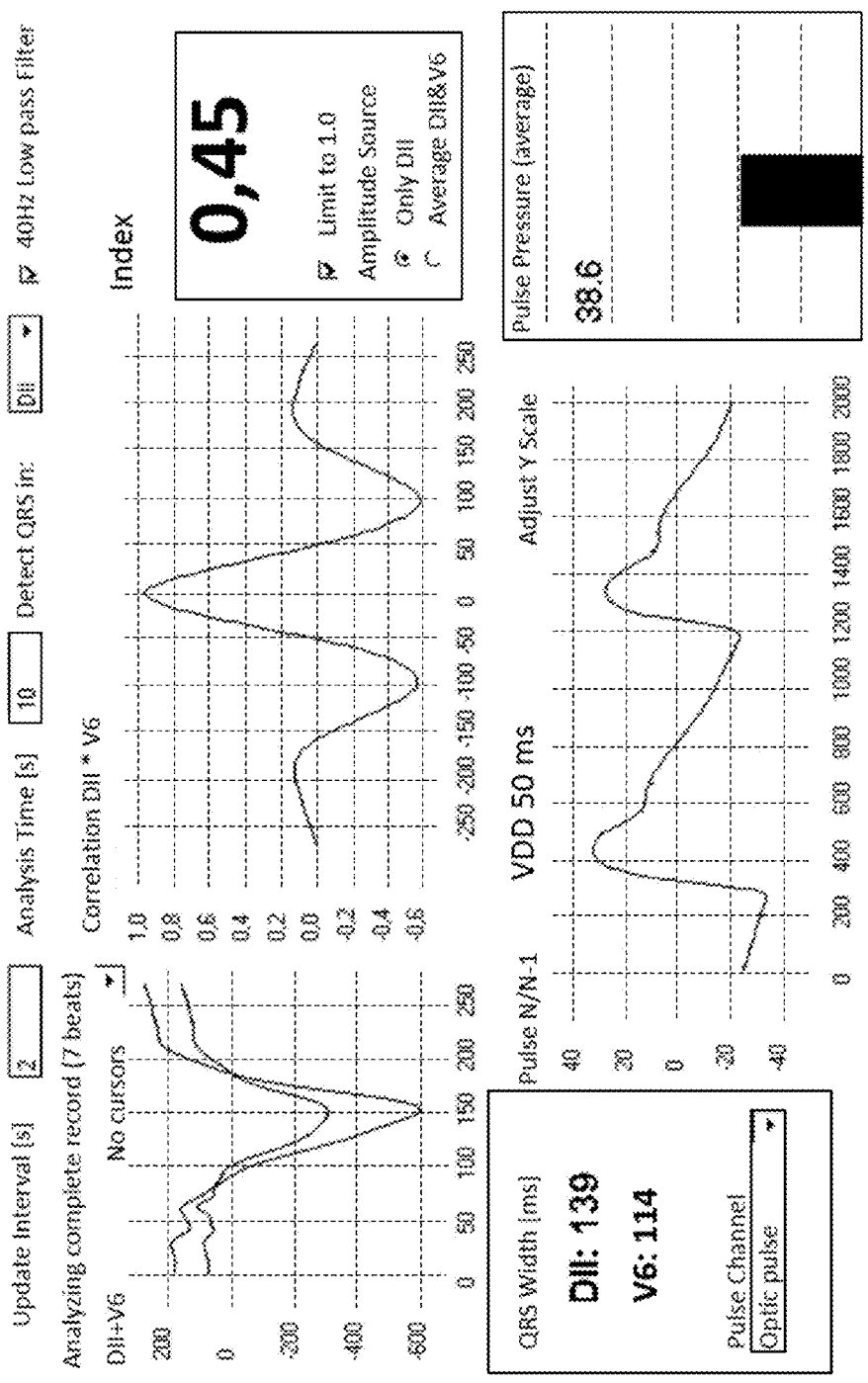
FIGS. 11A-11D show an example of sweeping AV delays in order to find the one producing the highest pulse wave amplitude, during right ventricular pacing in VDD (FIGS. 11A-11B) and DDD (FIGS. 11C-11D) modes, consistent with various aspects of the present disclosure.
Figure 11B:
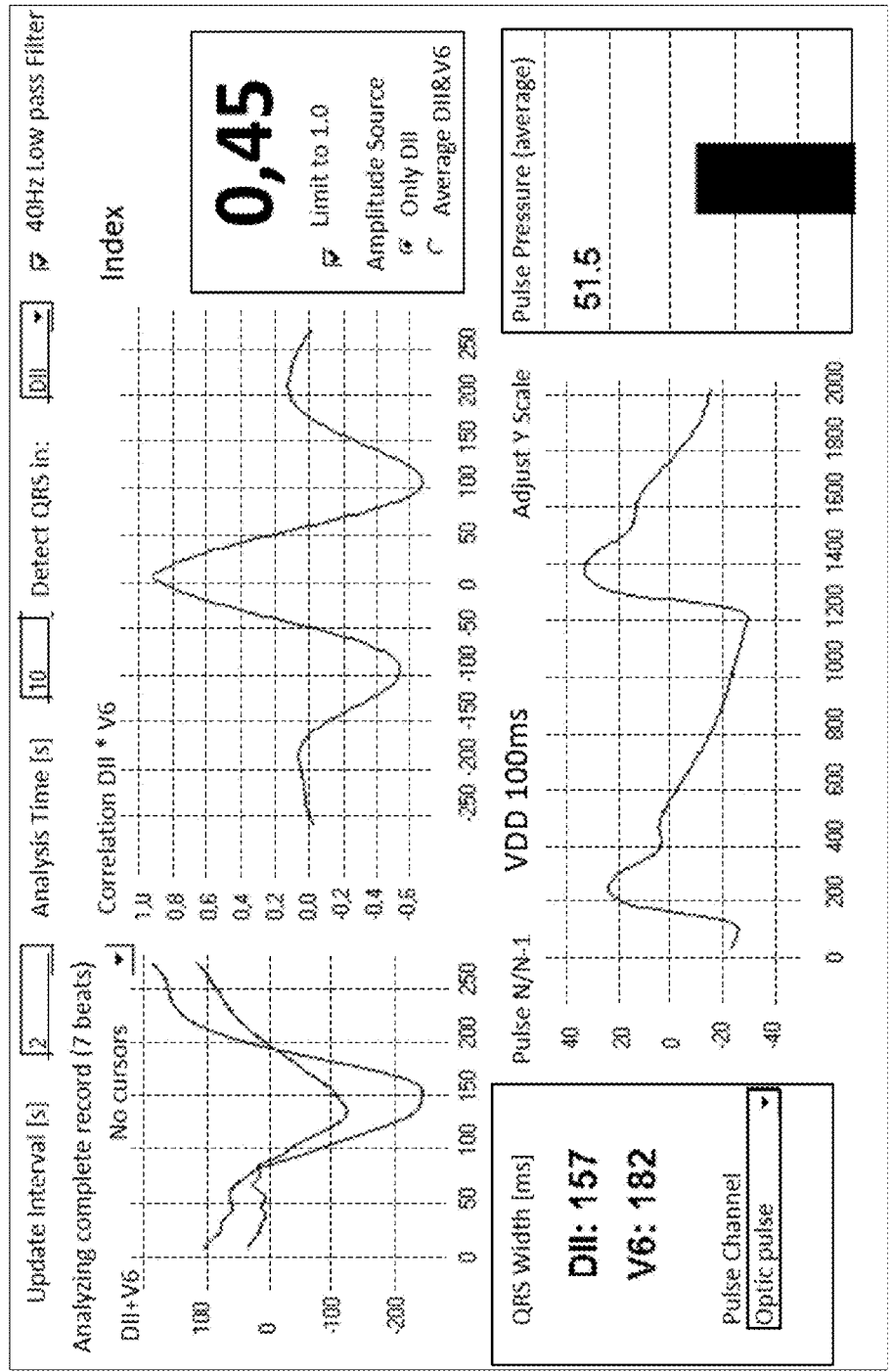
Figure 11C:
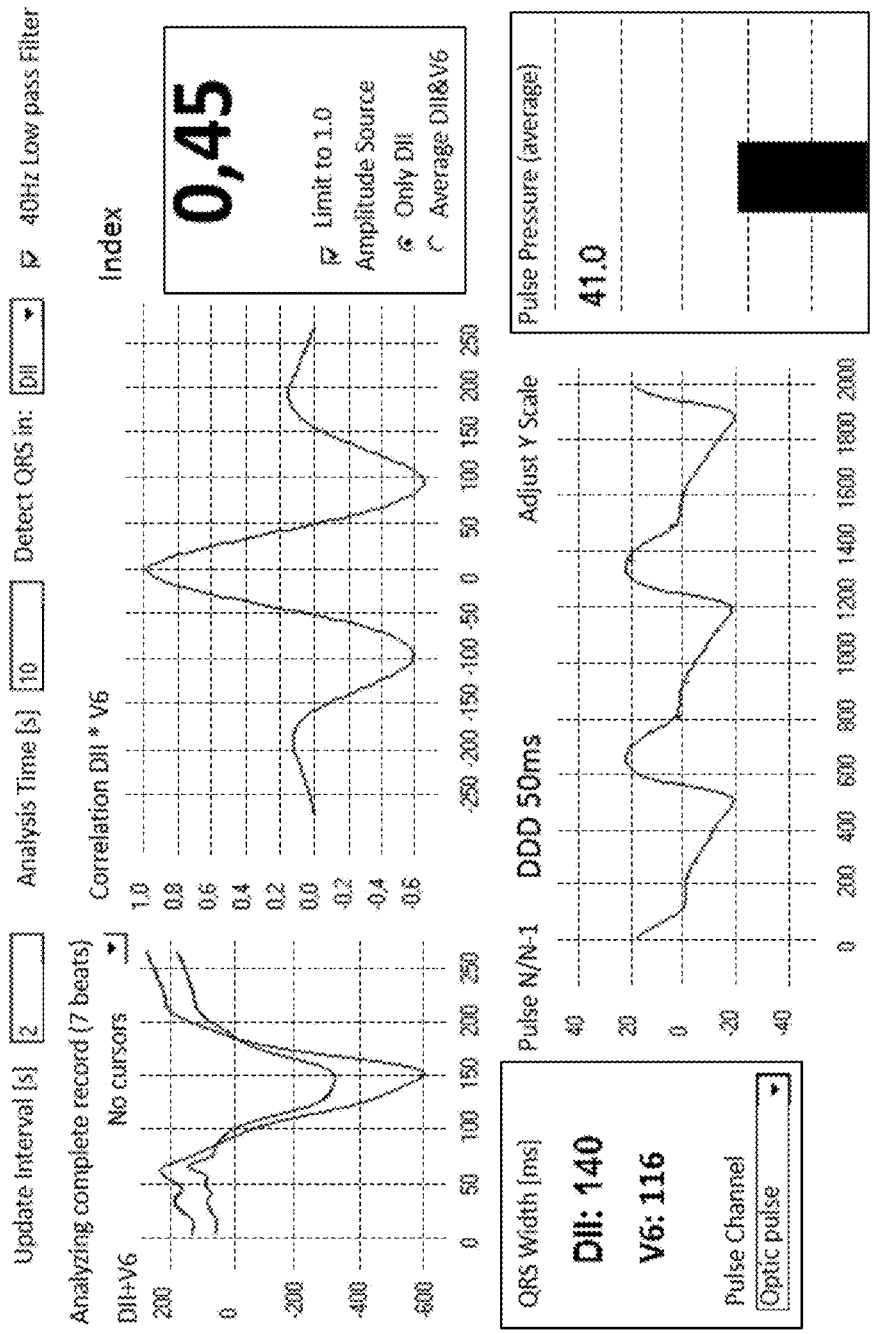
Figure 11D:
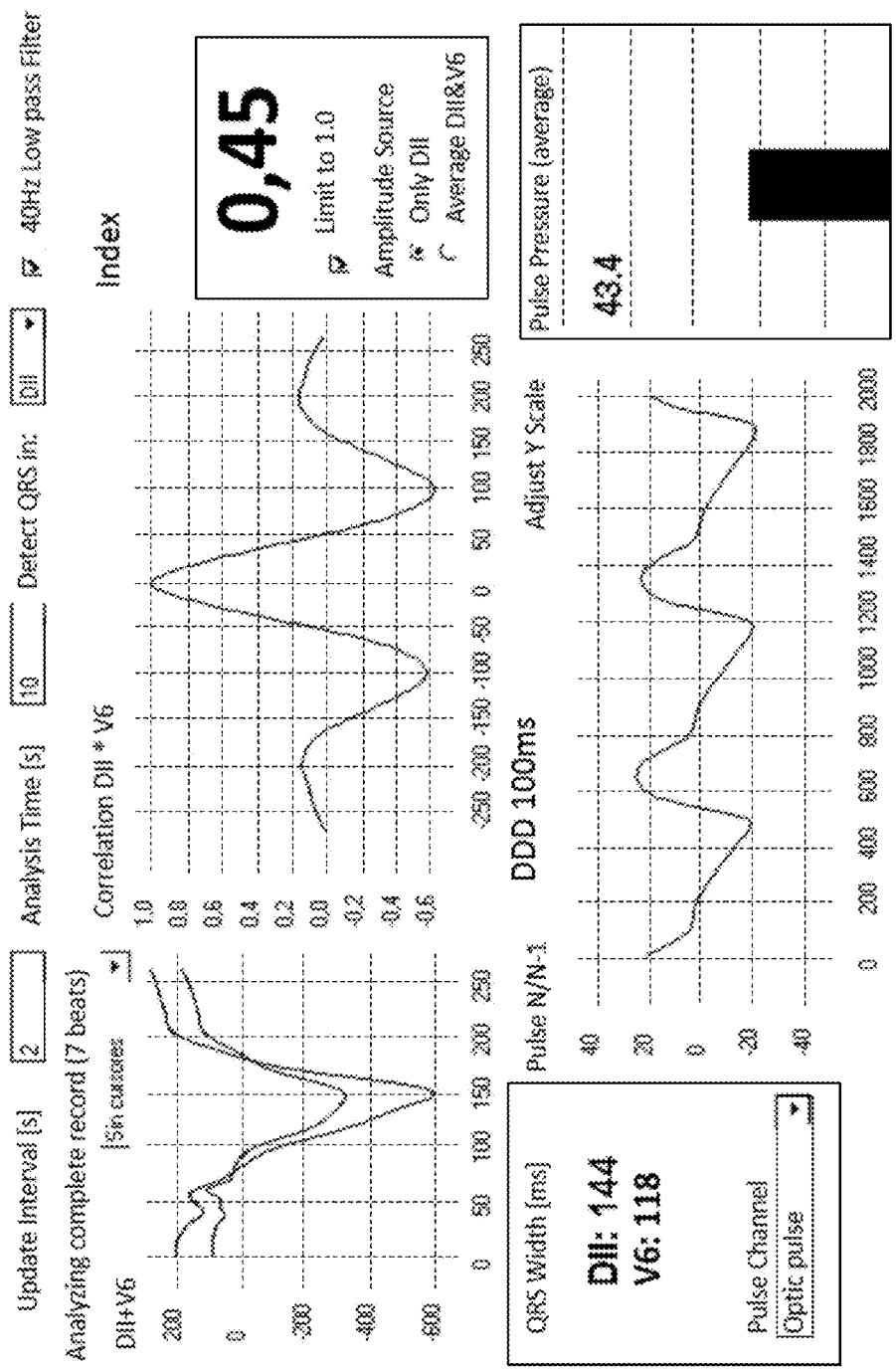

For example, FIGS. 11A-11D show the pulse pressure for 4 cases, VDD pacing at an AV delay of 50 ms in FIG. 11A, VDD pacing with an AV delay of 100 ms in FIG. 11B and the same AV delays for DDD pacing in FIGS. 11C-11D. FIG. 11A and FIG. 11C show an AV delay of 50 ms producing a weak pulse amplitude of 38.6 and 41.0 mmHg, for VDD and DDD pacing while FIG. 11B and FIG. 11D show a (better) AV delay of 100 ms pushed the pulse signal to 51.5 and 43.4 mmHg for VDD and DDD pacing. FIGS. 11A-11D also display the pulse wave and the bar next to it shows the pulse amplitude in numbers. The use of the pulse signal can provide optimization in embodiments of the present disclosure when there is none or minimal conduction through the AV node (thus the degree of electrical synchrony does not change with the different AV delays), or when it is desired to optimize cardiac preload with the AV delay rather than synchrony. This will also be true for cases where the optimum AV delay is so short that the ventricles are fully captured and there is no fusion between the intrinsically propagated activation through the AV node and the artificial pacing stimulation. This lack of fusion means that the activation dispersion will not be affected by changes in the AV delay and thus IEAI will remain constant while changing the AV delay at this short complete capture values. Furthermore, when the optimum AV delay is inside the range of complete capture with no fusion, AV delay optimization focuses on achieving the optimum preload for maximum ejected volume of the ventricles, while lead position and VV delays focus on obtaining the maximum possible level of synchrony of the contraction. Therefore our invention allows the implanting physician to optimize both parameters with regards to preload and synchrony independently in those cases.

Figure 12:
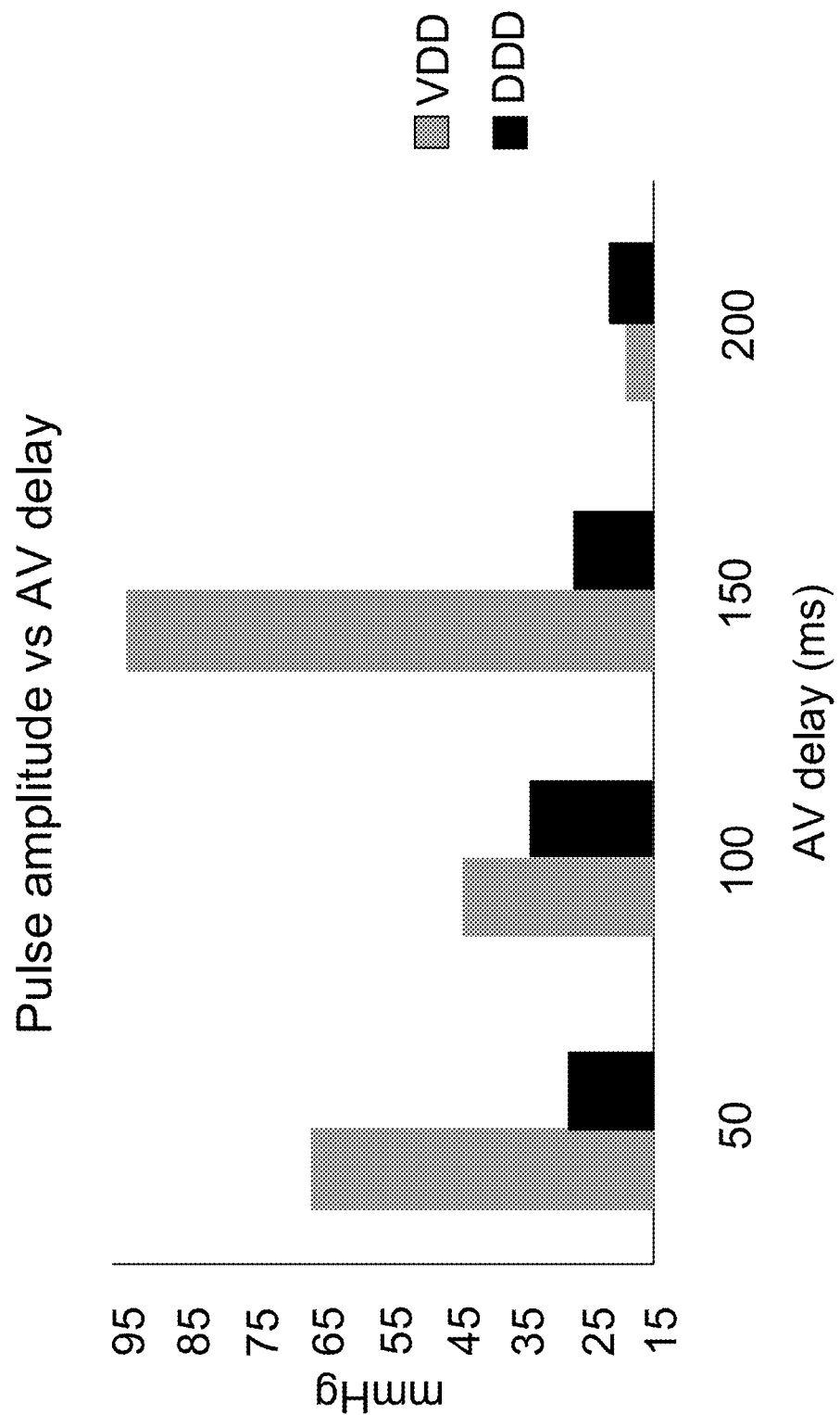
FIG. 12 shows a summary of the results obtained in a series of cases when sweeping AV delays in order to find the one producing the highest pulse wave amplitude, during RV pacing in the VDD and DDD modes, in accordance with various aspects of the present disclosure.

FIG. 12 illustrates the different pulse amplitude outcomes for four different AV delays for VDD pacing and DDD pacing. For most patients, VDD pacing produces better arterial pulse pressure results than DDD pacing. In the experimental results shown in FIG. 12, an AV delay of 150 ms and VDD pacing produced the highest pulse wave peak. This is likely due to the dispersion of the activation wave-front produced by artificially stimulating the atrium during DDD pacing (pacing both atrium and ventricle(s)) versus the more uniform activation of the atrium that occurs during normal activation with VDD pacing (sensing the atrium and pacing the ventricle(s)).

Figure 13:
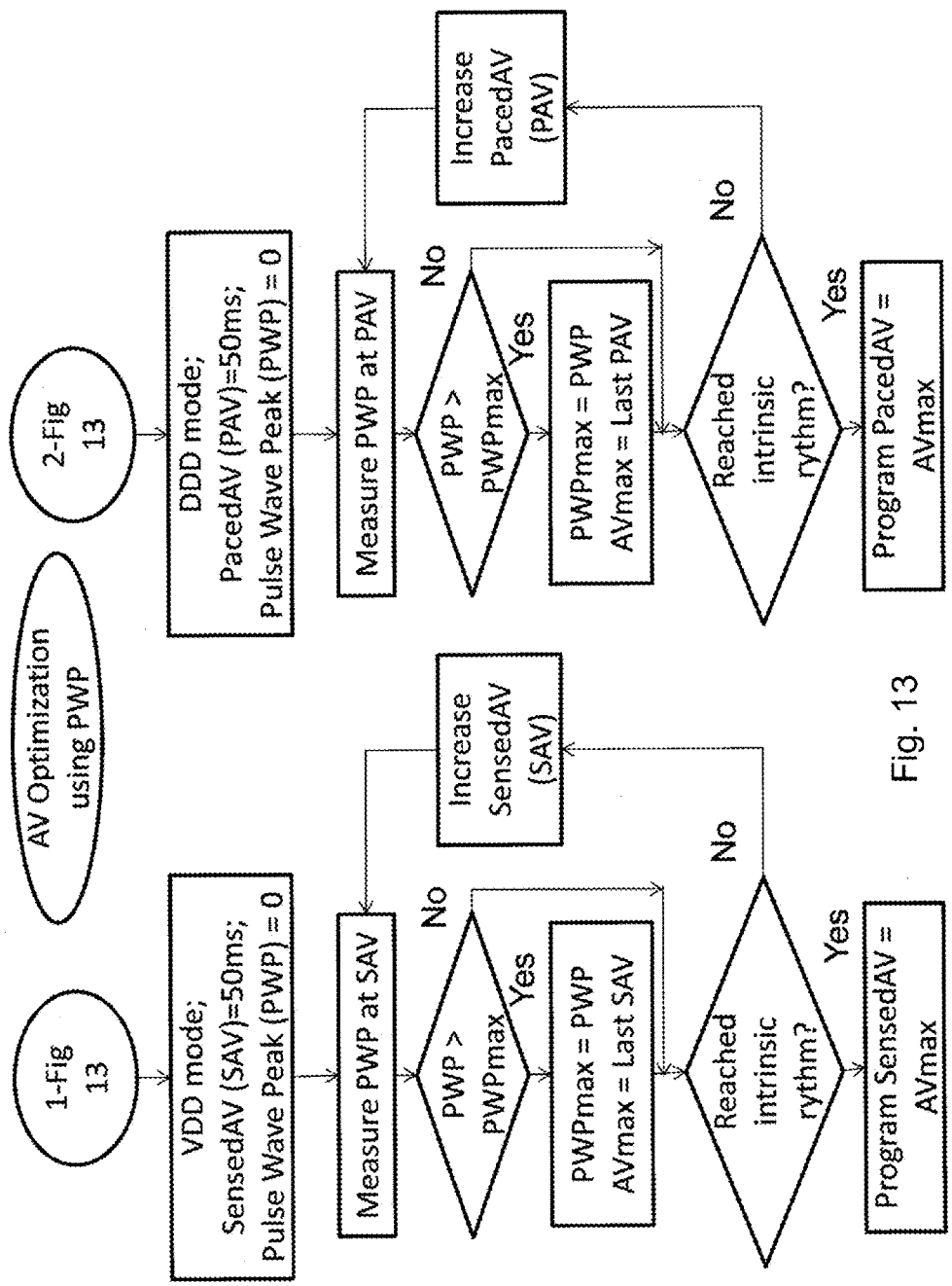
FIG. 13 shows an example flow diagram of AV interval optimization by pulse wave amplitude (PWP) in pacemakers programmed to VDD and DDD modes (left and right respectively), consistent with various aspects of the present disclosure.

FIG. 13 illustrates an example calculation for AV interval optimization in a pacemaker using arterial pulse pressure for optimizing preload conditions. Aspects of the present disclosure relating to AV interval optimization include choosing the rhythm (paced/sinus) that produces the best arterial pulse pressure (PWP). In this this case we optimize the PWP using an automatic adjustment of AV delay consisting of sweeping the AV interval in VDD mode to optimize the sensed AV interval by means of the pulse wave amplitude. In this procedure we also optimize the preload conditions of the heart by focusing on the maximum ejected volume produced using as a surrogate variable for ejection volume the arterial pulse pressure produced by the contraction of the left ventricle. The same procedure is then carried out for DDD mode. Further aspects of the present disclosure relating to AV interval optimization (not included in the figure for simplicity) include choosing the rhythm (paced/sinus) that produces the best IEAI; in this case we would be optimizing the synchrony level by adjusting with the AV delay the degree of fusion between the normally propagated activation waveform that comes from the AV node with the artificially triggered activation produced by the right, left and/or both leads.

Figure 14:
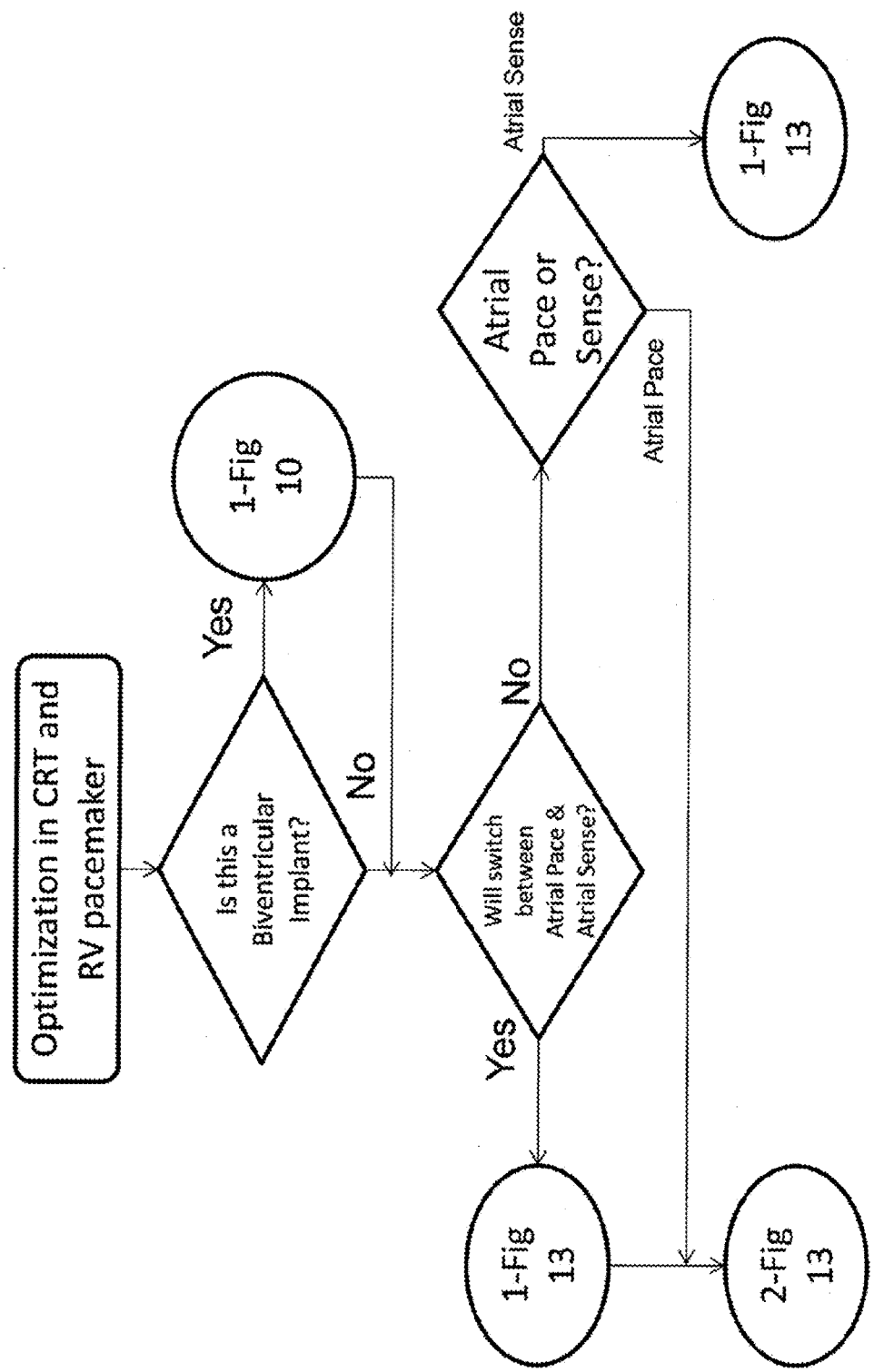
FIG. 14 shows an example of AV and VV interval optimization, by combining the examples provided in FIG. 12 and FIG. 13, in accordance with various aspects of the present disclosure.

FIG. 14 shows an example flow diagram for the optimization of a CRT and/or a pacemaker device (or the equivalent devices in a defibrillator). For a biventricular implant we first go through the flow diagram of FIG. 10, where the optimum VV delay is established, we then optimize the AV delay in either VDD or DDD modes or both using the example flow diagram of FIG. 13.

The optimum AV interval is the one that provides the largest average arterial pulse pressure. During AV delay optimization, the VV delay is fixed at the one that gave the lowest asynchrony index. Several different peripheral sensors can be used for the arterial pulse pressure measurement: for instance our prototype was implemented using the photoplethysmographic; the tonometric; and the oscillometric sensors. Other methods should be obvious to those skilled in the art. The measurement of the pulse wave provides indications of an optimal AV interval. This measurement can be utilized in embodiments having pacemakers or CRT devices. Additionally, the same indicator (pulse signal) can be used to adjust the VV interval in CRT implantations. In this case the operator needs to consider that changing the VV interval would change the AV delay, therefore the test should be conducted under VVI pacing at a constant rate, usually 10 bpm above the intrinsic rate should be adequate. Nevertheless, since VV interval affects mostly the dispersion of the activation wave-front and thus asynchrony the VV interval should be adjusted using the asynchrony index with the width of the AAQRSC as a secondary variable when needed, and not using PWP which is most sensitive to preload conditions and not necessarily synchrony. When the therapeutic target of asynchrony has been achieved with lead site and VV delay and therefore it is not required to attempt to tweak that level with creating a three way fusion between the artificial right and left pacing induced wave-fronts with the intrinsic activation that comes through the AV node, the AV delay should be optimized using the pulse signal. Furthermore, apparatuses, consistent with various aspects of the present disclosure, can be a tool capable of replacing the placement of a catheter into the coronary sinus to measure times between ventricular segments, either for diagnostic procedures or to determine therapeutic improvements in clinical follow-up.

Furthermore, apparatuses, consistent with various aspects of the present disclosure, can be a tool capable of telling the implanting medical personnel that a lead position in one site of the RV or the LV will provide a more synchronic electromechanical activation of the heart than a lead placed in another site. Furthermore, apparatuses consistent with various aspects of the present disclosure using the asynchrony index, the AAQRSC width or any combination of both will enable the implanting physician to know how far away in terms of asynchrony the particular lead placement achieved is from the therapeutic target that he/she has for that patient. Therefore, this enables a decision, during the implant, to consider other therapeutic options for that particular patient if the desired therapeutic target cannot be achieved. A particular example is a patient undergoing a right ventricular implant, in that case the asynchrony index will enable the implanting personnel to know if the degree of asynchrony being created by the artificial pacing spike in the right ventricle, at the site chosen by the physician meets his/her therapeutic target for that patient for not initiating or accelerating the progression towards heart failure that excessive asynchrony would trigger. If the physician cannot find an adequate right ventricular lead location, he/she may make the decision to upgrade the patient to a CRT or an XSTIM device.

Various aspects of the present disclosure are directed toward apparatuses having a self-contained device including a screen. This apparatus can be provided with a built-in printer or a connection to a printer in various embodiments. Further, apparatuses of the present disclosure include a device to which the ECG and arterial pulse sensor cables are connected. This device features an output that feeds a laptop computer containing the software protected by a software key. This device (e.g., a processor arrangement having circuitry) is configured to calculate an index to help find the optimal pacing site for any pacing device, with any lead configuration. Further, the device is configured to provide tools for AV-delay adjustment based on the pulse signal amplitude with application on DDD/VDD pacemakers and CRT devices, either automatically or manually. The device is also configured with tools for VV-delay adjustment based on the asynchrony index and/or the pulse signal amplitude with application on DDD/VDD pacemakers defibrillators and CRT and CRTD devices, either automatically or manually. Further, the device is configured to calculate an index to mark electrical intraventricular dyssynchrony in patients without pacemakers. The device, consistent with various aspects of the present disclosure, can also be configured to calculate an index to mark electrical intraventricular dyssynchrony in patients with pacemakers, and to determine candidates who will potentially benefit from CRT therapy. Additionally, the device is configured to allow the follow-up of patients implanted either with pacemakers or CRT devices, and can be integrated into a commercially available pacemaker, defibrillator or CRT device, or alternatively inside one of their programmers. Additionally, the device could transmit the information through radio frequency, through a network or using a standard or proprietary protocol to any means of remote devices, for instance a local server in the hospital or a remote server at a health care center where the follow up of the patient is done, or to a remote server of the manufacturer of the device being implanted for remote patient monitoring, follow up and/or management. The implanted device could be programmed to cycle through VV intervals or AV intervals inside a safety range pre-determined by the responsible medical personnel and the asynchrony index results could be derived inside the device using a calculated ECG from intracardiac electrograms, or transmitted to the remote devices and calculated in an external system. The resulting information could then be used to recommend an update of the VV or AV interval as the patient's condition evolves with time. This update could be programmed directly into the implanted devices through the communications protocol available or be informed to the responsible physician for update at the next follow up. Many alternatives and variations of this approach should be obvious to those skilled in the art.

Various embodiments are directed towards an apparatus consistent with aspects of the present disclosure combined inside a pacemaker or CRT or CRTD (CRT plus defibrillator) or pacemaker plus defibrillator. In these embodiments, ECG information can be obtained, processed, and displayed. Therefore, modification of the software of a pacemaker or CRT or CRTD (CRT plus defibrillator) or pacemaker plus defibrillator device can be made to implement various aspects of the present disclosure. Tweaks and adjustments to the front end filters, digitalization rates and digital signal processing capabilities can be made.

Additionally, apparatuses of the present disclosure, in various embodiments, can be implemented (without the His or the arterial pulse capabilities) inside the software of the pacemaker CRT or CRTD (CRT plus defibrillator) or pacemaker plus defibrillator. In these instances, the ECG is replaced by a pair of leads formed by the available electrodes in the defibrillator, pacemaker, CRT or CRTD device that best resembles as a pseudo ECG lead (such as Lead II and V6), or a representation of the inferior frontal side and the lateral wall of the left ventricle.

Further, an asynchrony index (IEAI), consistent with various aspects of the present disclosure, is implemented in an iPad®, iTablet®, or smart phone (e.g., a smart device). The ECG information is gathered by separate hardware, sent to the smart device through blue tooth, WiFi, WiMax, G3, G4, G5 or other cellular protocol and then processed and displayed by the smart device. The smart device can also store the information on the Cloud for people to keep a record of their asynchrony index or for physicians or care providers to monitor the patient's health status or adjust their therapy, including drug adjustments. This will make a diagnosis of asynchrony much easier and allow for earlier interventions (diet, lifestyle, stress, tobacco, etc.) that may even be able to prevent and preempt the need of device implantation to correct it. Since it is reasonable and even expected that the morphology and status of the patients heart will change with time after the office visit, the device could be allowed to automatically try different VV or AV intervals (small changes pre-programmed by the intervening medical personnel) and report the information on the asynchrony index, information that could be further used to reprogram the baseline value of the VV or AV delay of a CRT device remotely or locally with physician or medical personnel approval once a recommendation is made by the device. Furthermore, the ECG hardware could be miniaturized and attached to the patient temporarily or chronically either subcutaneously or on the skin, directly or through a special shirt or underwear, equipped with disposable or rechargeable batteries and communicate through low power blue tooth or other communication protocol with the external system that may fully reside inside an iPad, tablet or smart phone or similar device. The external device could act as the display unit or as a full processing unit calculating the index by itself or remotely in the cloud or both. The data could be stored locally or on the cloud.

Various embodiments of the present disclosure are directed toward acquiring data from an ECG, and to providing the data for analysis by a patient or health care specialist. The ECG data can be acquired locally (e.g., in the physician's office, patient's home, ambulance, hospital, ambulatory) and transmitted to a remote location. In this manner, any number of physicians/nurses/technicians can analyze the data acquired (assuming appropriate authorization is given). For instance, a data interface can be used to upload the ECG data to a remote device. A patient or health care specialist can then review the data. This reviewed data can be used in developing a program of VV or AV delays that minimizes asynchrony, which can include additional treatment options, and/or adjustments. Information other than, or in addition to, ECG data can also be acquired and uploaded.

Furthermore, certain embodiments contemplate that for devices with activity sensors a correlation can be made between the optimum VV or AV intervals during different levels of activity such that a table could be created inside the device that would allow the adaptation of the VV or AV interval to the level of activity measured. Activity sensors can be of several types, from minute ventilation sensors that track the change in respiratory activity created by exercise to simple accelerometer sensors that track changes in acceleration in one or multiple axis. In still another embodiment the sinus rate detected by the atrial lead is used to gage the activity level and correlate the optimum VV or AV interval with the heart rate at which the optimization occurred. All these analysis can be performed inside the device or outside the implanted device by an external system that could return the recommended programming to the device in a simplified format, i.e. a table with sensed atrial rates and optimum VVs or AVs for each rate range, for the implanted device, such external analysis will minimize the device hardware/firmware requirements and power consumption.

Certain embodiments contemplate a wired interface for uploading the information. The interface can include one or more standardized interfaces (e.g., USB or Firewire) or proprietary interfaces. For example, the system can include a USB circuit that is configured to operate as a USB peripheral device. A USB cable, with USB connectors, can connect the system to a remote processing device (e.g., a laptop computer, tablet computer or personal computer). The acquired data can be automatically uploaded using software drivers and/or the system can appear as a storage device (e.g., flash drive) upon which the acquired data is stored.

Various embodiments are directed toward a wireless interface for uploading of the acquired data. The wireless interface can be configured for use with various standardized protocols (e.g., Bluetooth, IEEE 802.11xx, cellular protocols, near field communications, far field RF communications or WiMax). In certain embodiments, the wireless circuit for the interface can be configured to conserve power by powering down or entering a low power state between uploading, like low power Bluetooth or its power saving schemes.

Consistent with one or more embodiments, access to the acquired data can be limited to authorized persons. This can include, for example, the use of encrypted communications and/or password protection.

Consistent with one of more embodiments the device can be completely implemented either inside an ECG machine or inside a programmer for pacemakers, defibrillators and/or CRTD devices.

Figure 15:
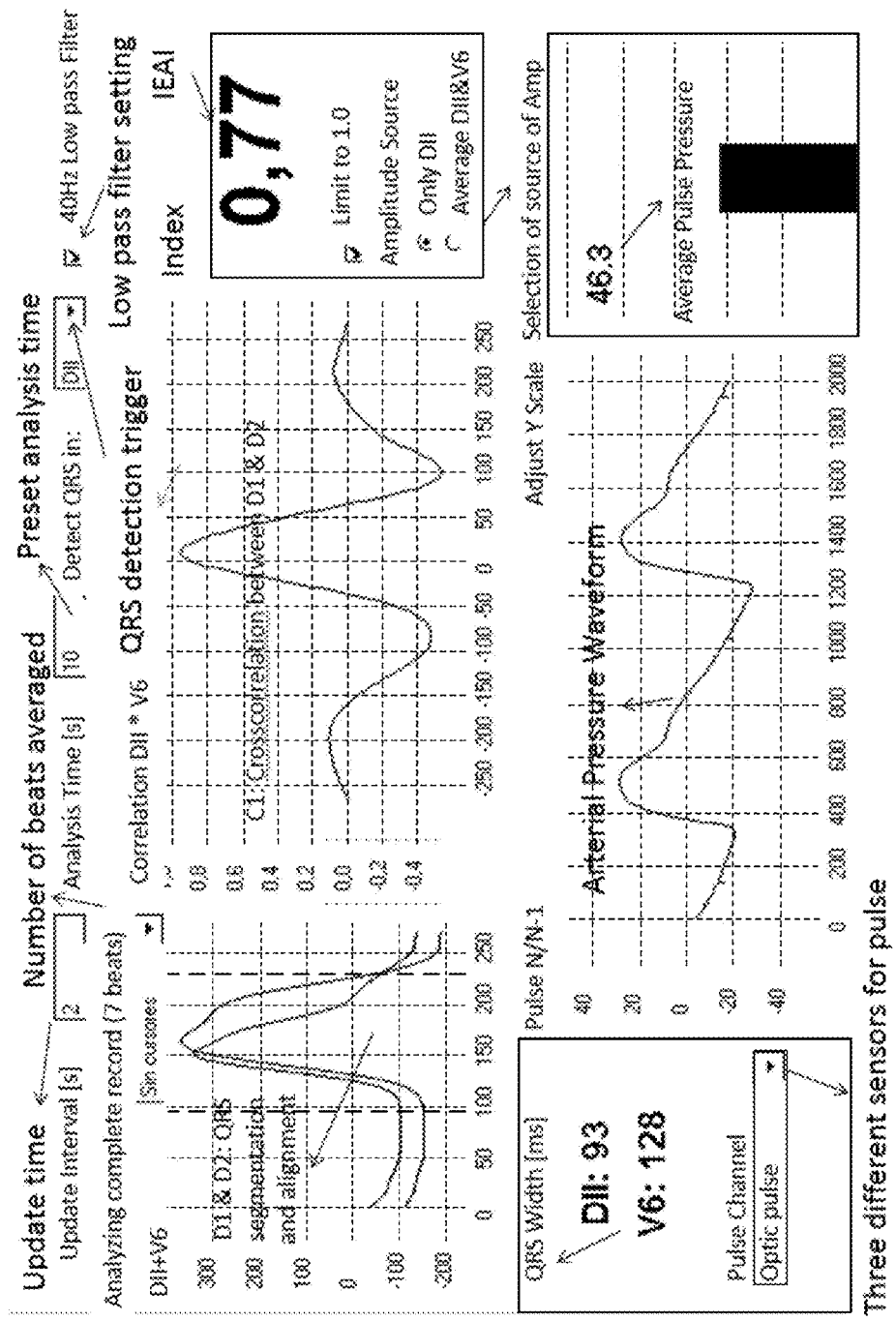
FIG. 15 shows an example of a possible interface implementation, currently implemented in a prototype apparatus showing multiple features, consistent with various aspects of the present disclosure.

FIG. 15 shows an example interface of an apparatus, consistent with various aspects of the present disclosure, showing a feature to measure QRS durations. The upper panel shows two sets of calipers marking the start and end of both QRS complexes. The calipers can be turned on or off by selecting the correct option in the drop down menu above the ECG window. The update time selects the interval between new readings of the IEAI index and other variables displayed. The number of beats averaged window indicates the number of beats that have been used to calculate the average value of the pulse pressure. This number is represented by the green bar at the bottom right of the window. The large red number in the top right side is the IEAI 0.77. Right beneath the IEAI are the selection buttons for the source of Amp in the IEAI equation. For the IEAI numbers reported in this disclosure we have used the "lead II" selection. The drop down menu on the top right is the filter setting selector. The preset analysis time determines the time sample of the ECG and pulse pressure used for the analysis. The QRS detection trigger defines what lead D1 or D2 is used for the detection of the complex. The waveform in the top right window is the Cross-correlation between D1 and D2. The waveforms in the top left window are the QRS complexes of the D1 and D2 leads (in this case lead II and V6). The numbers underneath are the QRS widths DII in green 93 ms because it is below 100 ms and V6 in red 128 ms because it is over 120 ms. The drop down selection menu underneath these readings selects the type of sensor used for the acquisition of the arterial pressure waveform. Finally in the bottom center of the window you find the arterial pressure waveform. It should be obvious that those skilled in the art could come up with a myriad of other possible display interfaces that would still be covered by this invention.

Figure 16:
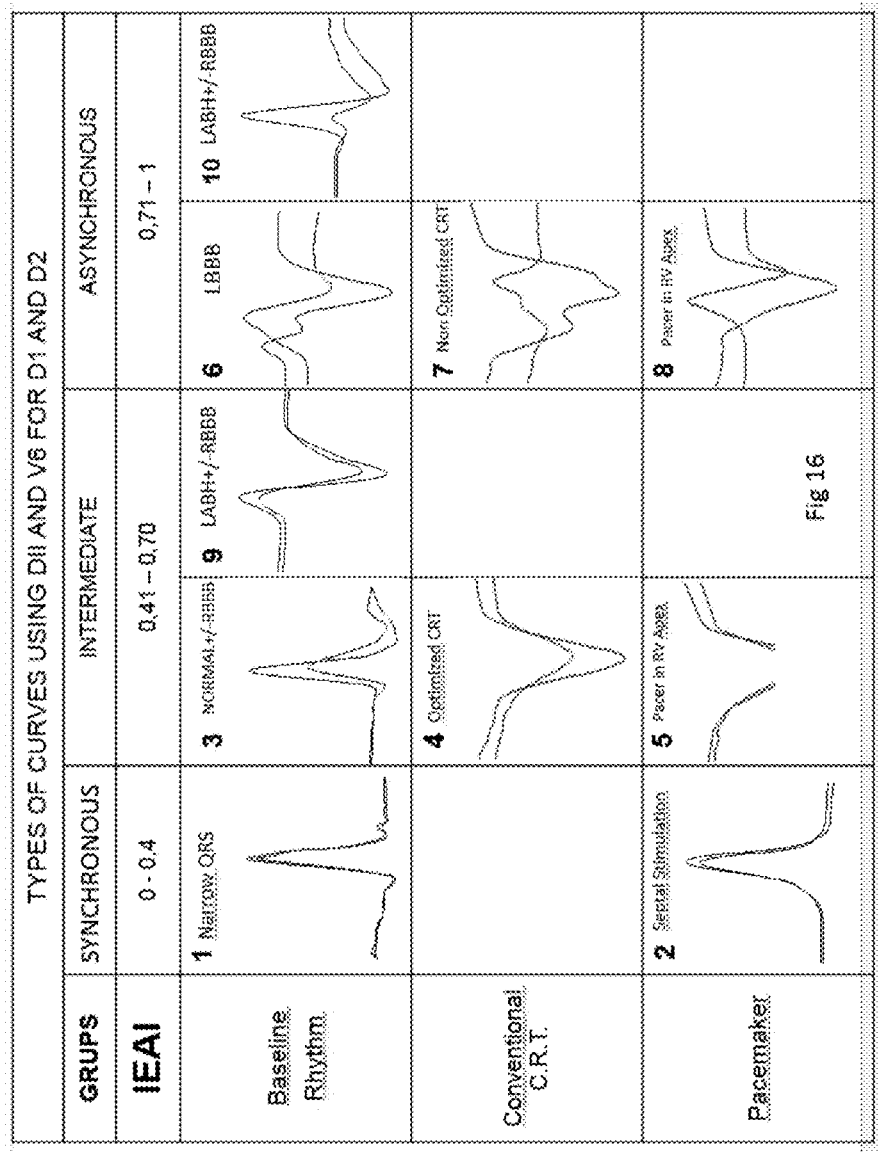
FIG. 16 shows examples of the ten curve types and IEAI ranges in which we have classified clinical patients when D1 and D2 are lead II and V6, consistent with various aspects of the present disclosure.

An example of the patient classification that can be performed using the D1 and D2 curves and the IEAI number is shown in FIG. 16 for the particular coefficients $a_i$, C, sample rate, etc. described in the present disclosure as used in our prototype system. The different columns cover the following classes: 1) Synchronous ($0 \leq IEAI \leq 0.4$); 2) Intermediate ($0.41 \leq IEAI \leq 0.70$); and 3) Asynchronous) ($0.71 \leq IEAI \leq 1$). The intermediate patients are further subdivided into a) normal conduction with and without right bundle branch block (RBBB) and b) left anterior branch hemi block (LABH) with and without right bundle branch block (RBBB). The asynchronous patients are divided into the left bundle branch block (LBBB) and the LABH with and without RBBB. For each column we have three rows, in the first row we depict the curves for baseline rhythm (no pacing), which create curve type 1 for the synchronous type, curve 3 for the intermediate type with normal conduction with and without RBBB, curve 9 for the intermediate type with LABH with or without RBBB, curve 6 for the asynchronous type with LBBB and curve 10 for the asynchronous type with LABH with or without RBBB. The second row corresponds to the conventional CRT therapy (biventricular pacing), which creates curve 4 for the intermediate column and corresponds to optimized CRT therapy and for the asynchronous column, the non-optimal CRT creates curve 7. The third row is for pacemakers, curve 2 is created by septal stimulation, curve 5 (intermediate) and curve 8 (asynchronous) are created by apical stimulation.

Figure 17:
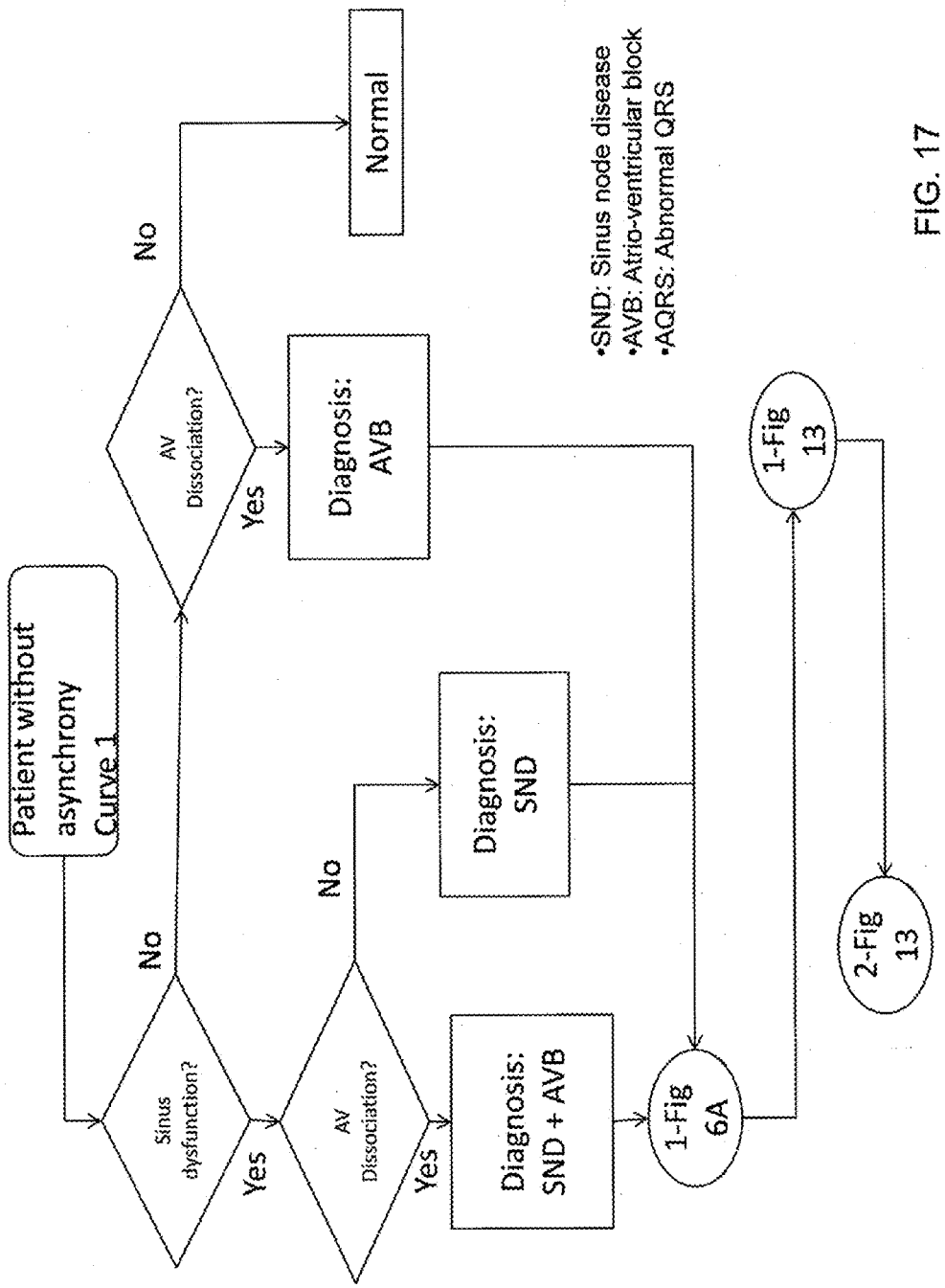
FIG. 17 shows an example flow diagram of how to use some of the embodiments of the present disclosure to optimize the therapy delivered to a patient that doesn't have baseline asynchrony (IEAI<0.4 and curve 1 from FIG. 16), but may be indicated for a pacemaker or defibrillator implantation, consistent with various aspects of the present disclosure.
Figure 18:
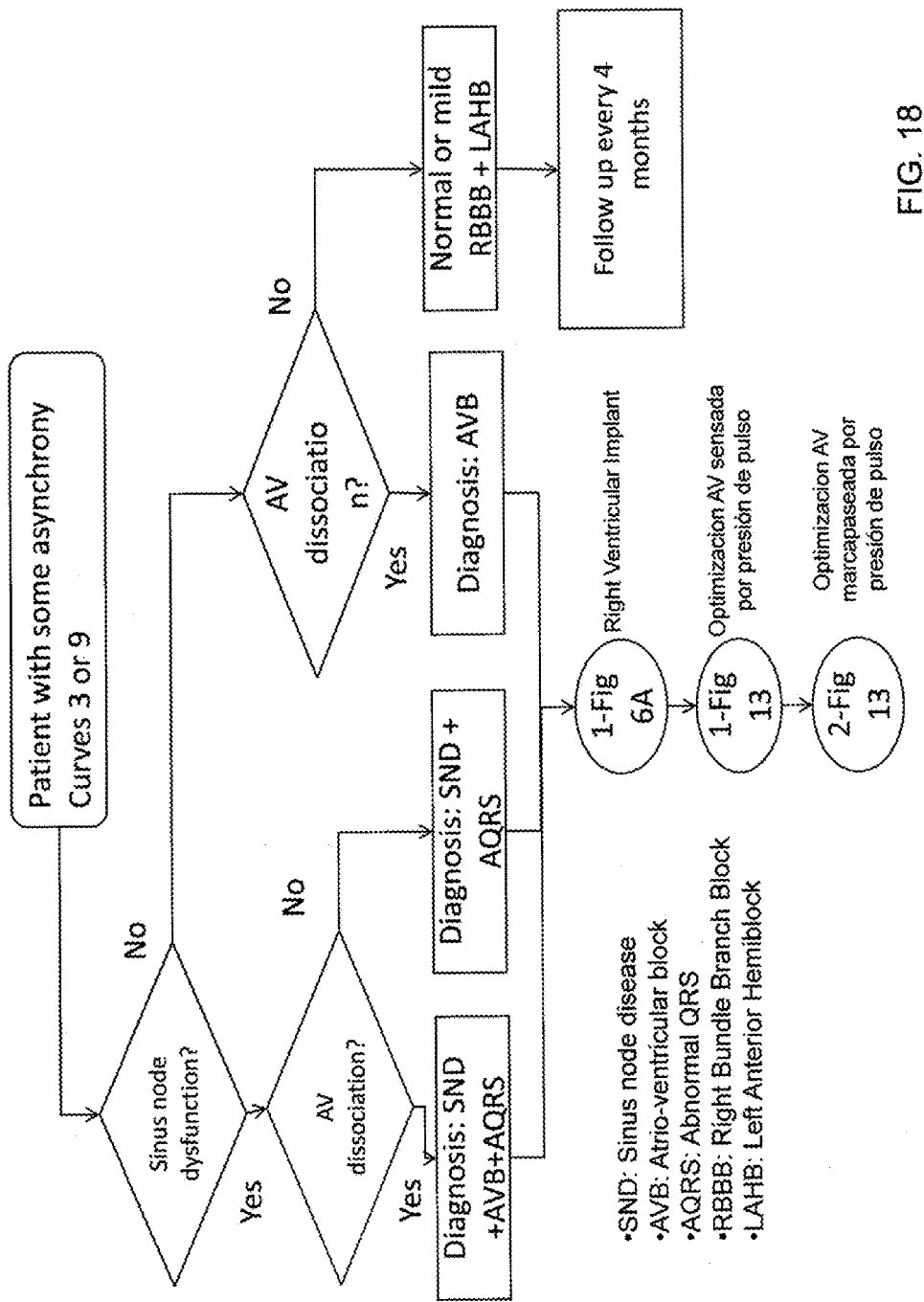
FIG. 18 shows an example flow diagram of how to use some of the embodiments of the present disclosure to optimize the therapy delivered to a patient that has some asynchrony (0.41<IEAI<0.70 and curve type 3 or 9 in FIG. 16) and may be indicated for a pacemaker or defibrillator implant, consistent with various aspects of the present disclosure.
Figure 19:
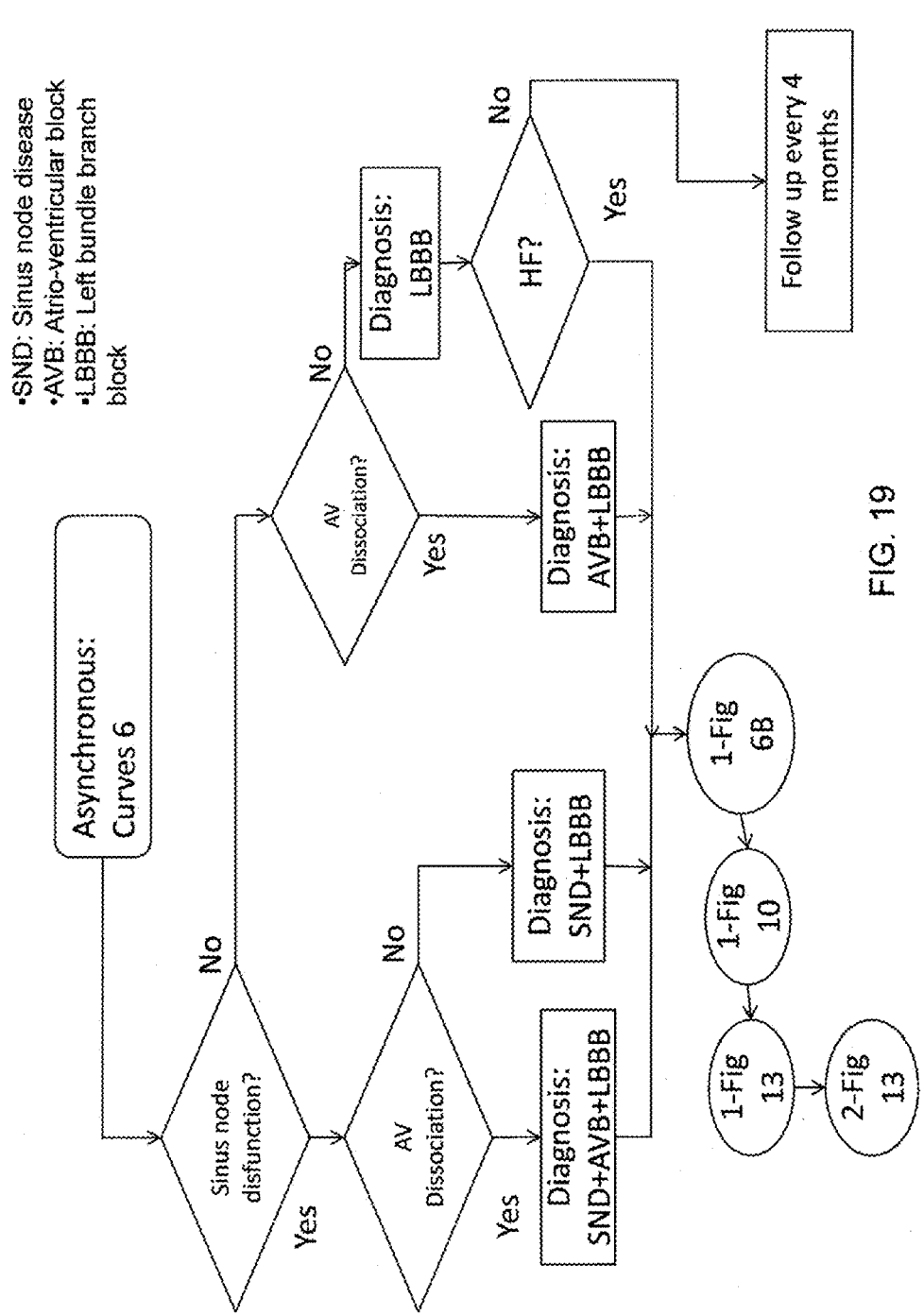
FIG. 19 shows an example flow diagram of how to use some of the embodiments of the present disclosure to optimize the therapy delivered to a patient that has asynchrony (IEAI>0.71 and curve type 6 in FIG. 16), and may be indicated for a device implant, consistent with various aspects of the present disclosure.
Figure 20:
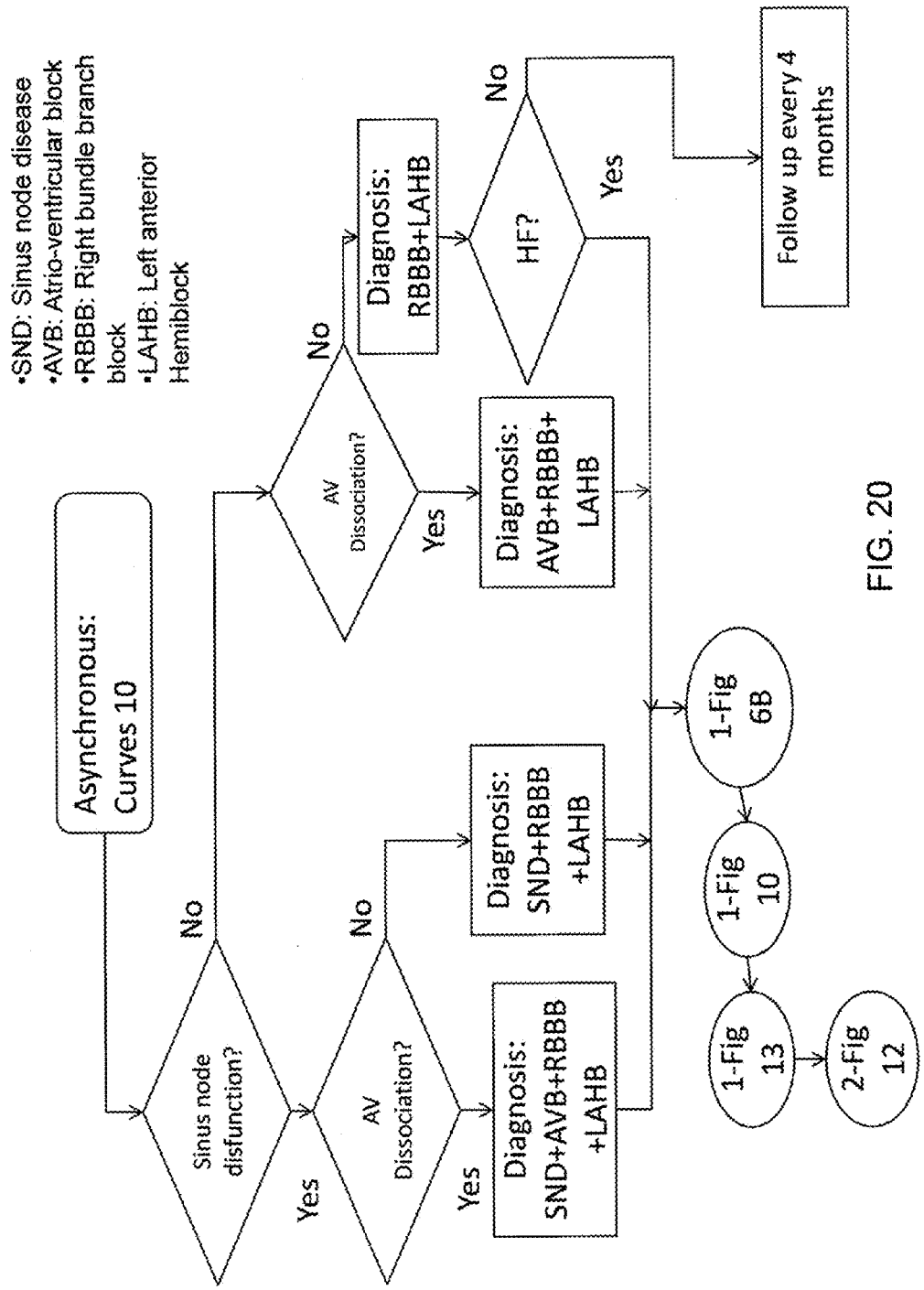
FIG. 20 shows an example flow diagram of how to use some of the embodiments of the present disclosure to optimize the therapy delivered to a patient that has baseline asynchrony (IEAI>0.71 and curve type 10), and may be indicated for a device implant, consistent with various aspects of the present disclosure.

FIGS. 17 to 23 summarize in a simplified flow diagram the process of diagnosis and application for each diagnosis of the different algorithms mentioned in the present disclosure. FIG. 17 corresponds to patients with no asynchrony and curve type 1. If they are indicated for a pacemaker implant then the diagram indicates that the lead selection process described in FIG. 6A should be used, followed by the AV delay optimization procedure described by FIG. 13. FIG. 18 applies to patients with curve types 3 or 9 and some asynchrony. The diagnosis would be different but the approach to follow the same as in FIG. 17. The simplified diagram of FIG. 19 contemplates the implantation of a left ventricular lead thus flowing through the RV lead implant optimization (FIG. 6A) followed by the LV lead site optimization (FIG. 6B), the VV optimization (FIG. 10) and the AV delay optimization (FIG. 13). The flow for FIG. 20 despite different diagnosis than FIG. 19 ends up with the same procedure as in FIG. 19.

Figure 21:
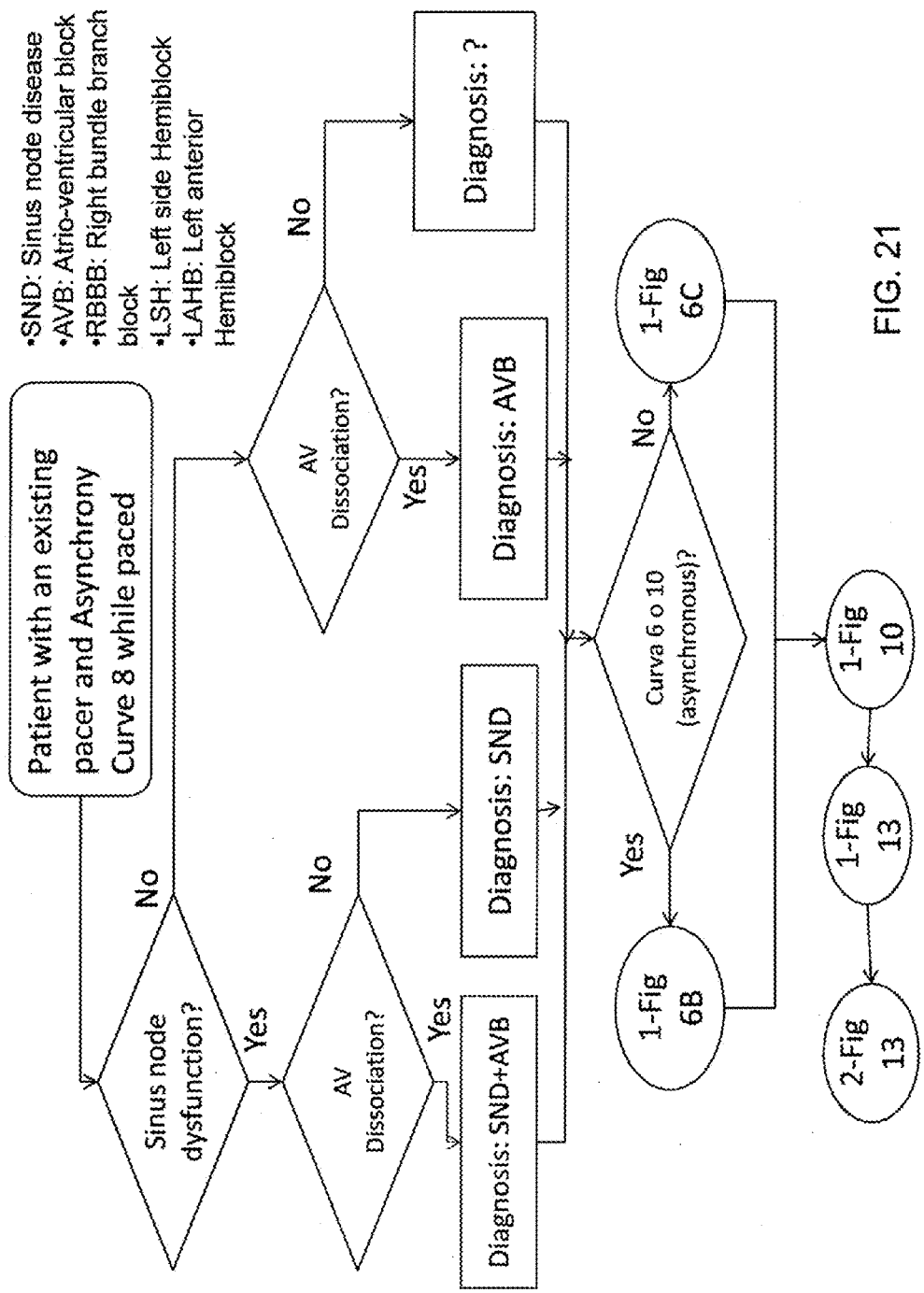
FIG. 21 shows an example flow diagram of how to use some of the embodiments of the present disclosure to optimize the therapy delivered to a patient that already has an implanted pacemaker and asynchrony (IEAI>0.71 and curve type 8) when paced in the right ventricle, consistent with various aspects of the present disclosure.

The case for a patient that has an existing implanted lead and pacemaker with curve 8 during pacing and asynchrony is depicted in FIG. 21. In the case where the patient also has asynchrony (curves 6 or 10) at baseline (without pacing) the flow ends up with the upgrade to a CRT device with left and right ventricular pacing. The patient could also be indicated an XSTIM device in lieu of a CRT device. If the patient baseline is not asynchronous, then a septal lead position for the RV is recommended plus a CRT device with the septal lead connected to the LV port of the CRT device and the old lead connected to its RV port, or an XSTIM device.

Alternatively, in the cases of FIGS. 17 to 21, a pacemaker using high voltage output to stimulate the His bundle and bypass the conduction block, similar to those described by patents US007512440, US008005544, US008014861 and US008050756 and applications 20120101539 could be utilized (XSTIM). In this last case the IEAI will allow the operator to detect when the His bundle position is achieved since its value will drop to near zero and the curve type would be 1. And only the RV site optimization flow diagram of FIG. 6A or 6C could be used with the lead on the septal side. In this case the target site is known, the His bundle, and the IEAI could be used to confirm it has been located.

Figure 22:
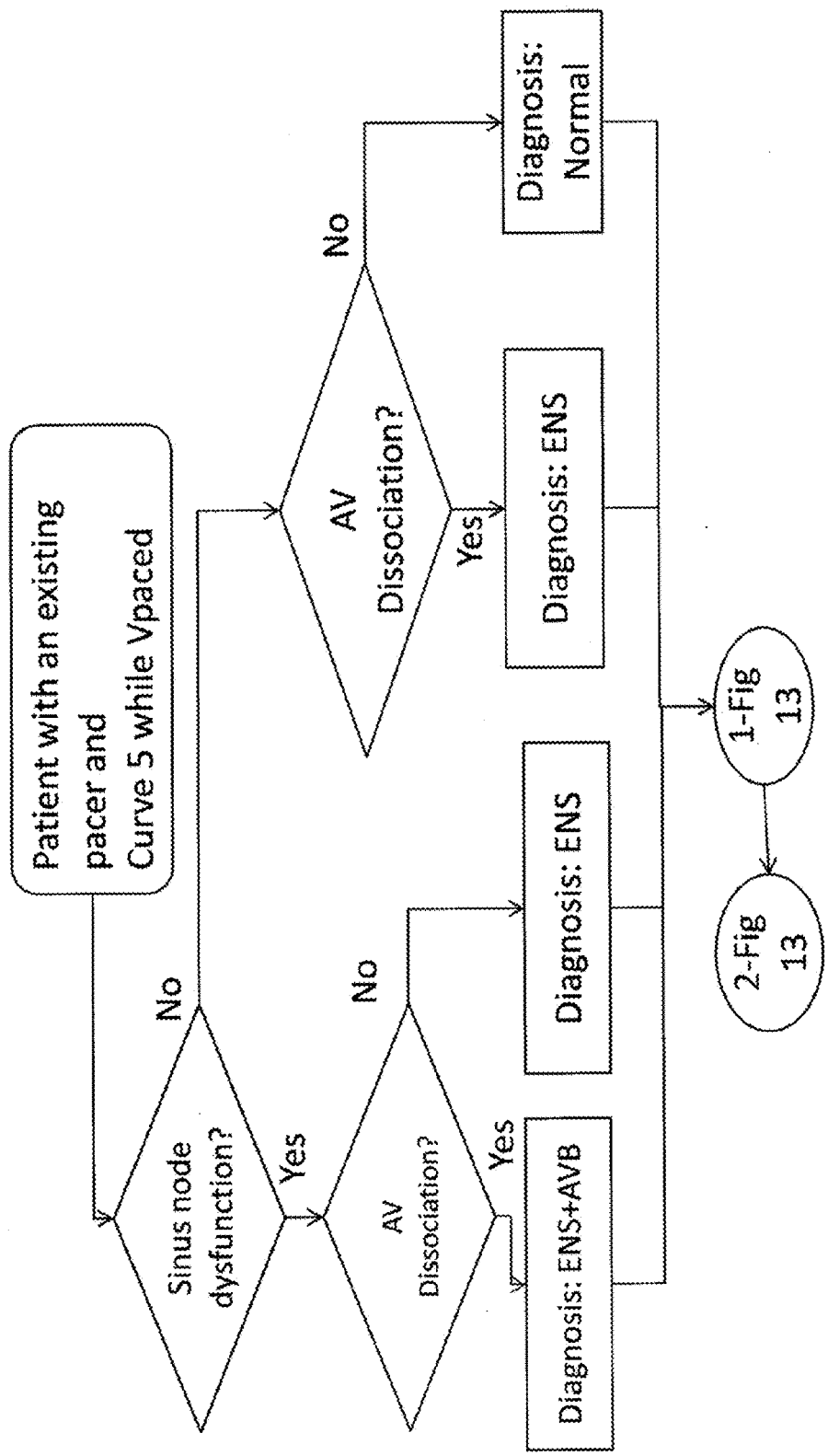
FIG. 22 shows an example flow diagram of how to use some of the embodiments of the present disclosure to optimize the therapy delivered to a patient that already has an implanted pacemaker and asynchrony (0.41<IEAI<0.70 and curve type 5) when paced in the right ventricle, consistent with various aspects of the present disclosure.

FIG. 22 contemplates a patient that has an existing pacemaker and lead implanted and intermediate asynchrony with curve type 5 while paced in the ventricle (Vpaced). For this case only the AV delay optimization algorithms of FIG. 13 would be used.

Figure 23:
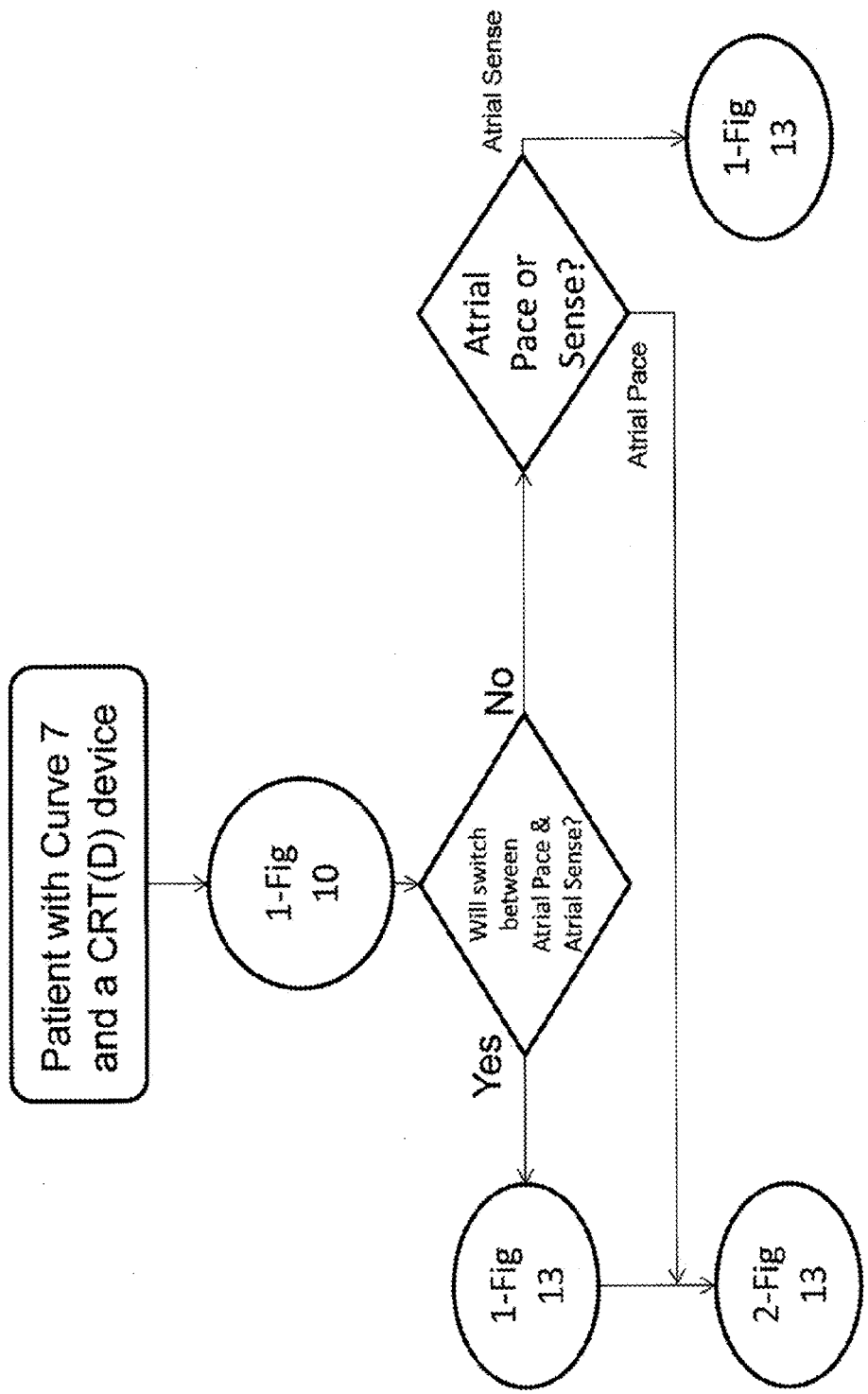
FIG. 23 shows an example flow diagram of how to use some of the embodiments of the present disclosure to optimize the therapy delivered to a patient that already has an implanted CRT or CRTD device and asynchrony (IEAI>0.71 and curve type 8) when paced in both ventricles, consistent with various aspects of the present disclosure.

Finally, the case where a CRT device is implanted and pacing both right and left ventricles (BV) in a non-optimized way is described by FIG. 23, where a patient with asynchrony and curve 7 while BV paced is contemplated. For this patient, the VV delay optimization algorithm of FIG. 10 is used first and then the corresponding AV delay optimization algorithms of FIG. 13.

Figure 24:
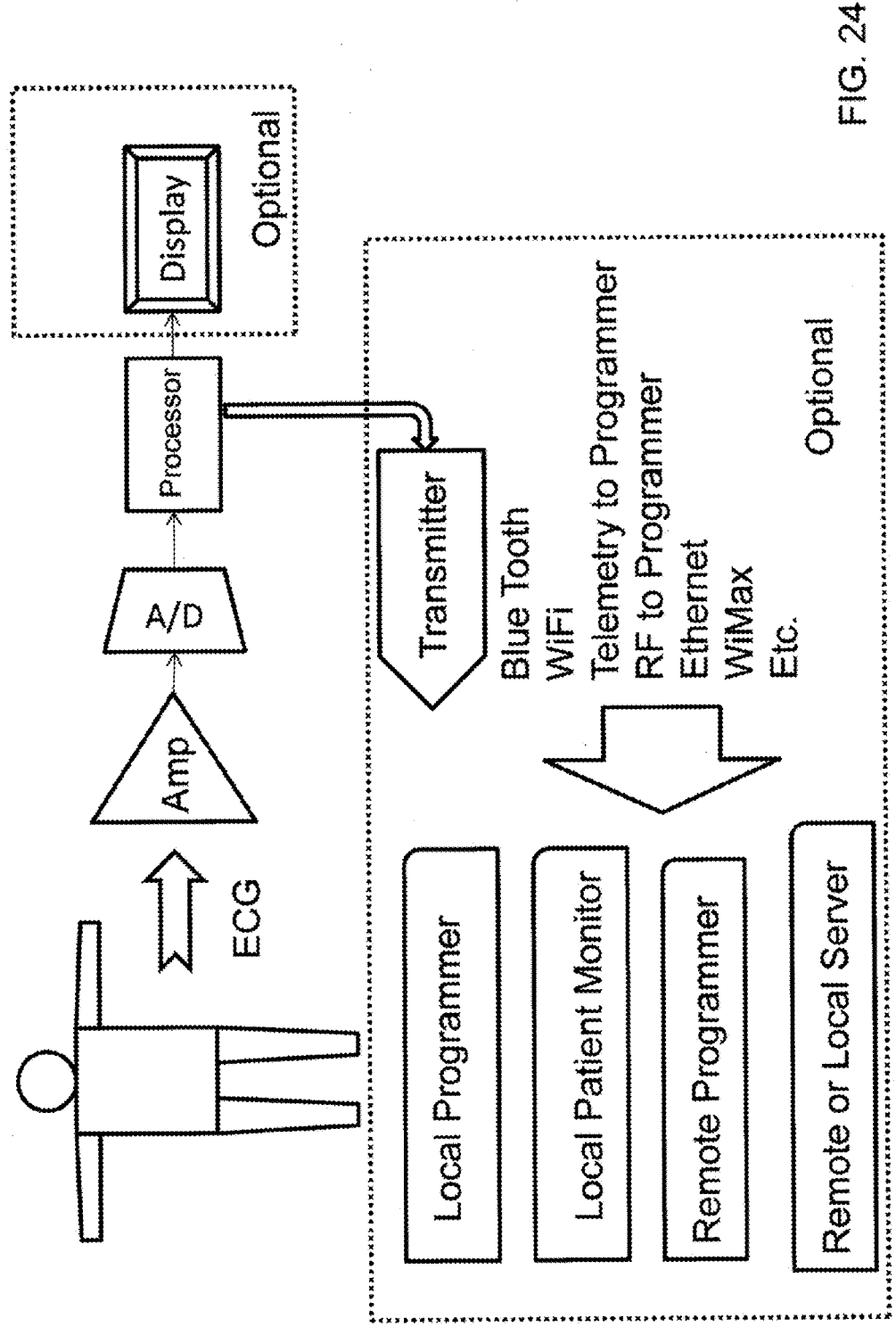
FIG. 24 shows an example block diagram of a possible implementation of the asynchrony index (IEAI) calculation and display and how this information set could be shared with a local programmer, a remote programmer, a local or remote server, or a patient management and/or monitoring box for further processing, analysis, monitoring or action (i.e., reoptimization of the VV delay) triggered by the local or remote systems with or without the supervision and approval of intervening medical personnel, in accordance with various aspects of the present disclosure.

FIG. 24 shows an apparatus connected to a patient to extract the ECG through leads or some form of telemetry from a device attached to the patient or implanted subcutaneously. The information is then sent to an amplifier having an output which drives an optional analog to digital converter for presenting the approximated signal to a software-programmed processor (e.g., CPU) where the signals are conditioned and analyzed and the IEAI extracted. In certain embodiments, the least significant bit of the output signal from the A/D (analog-to-digital) converter refers back to the voltage of the input of the ECG amplifier. The specific (amplifier) gain can vary, for example, relative to the A/D settings. In one such embodiment, the least significant bit of the A/D (analog-to-digital) converter represents 1.9531 microvolts at the input of the amplifier. The bandwidth can be inferred from the sampling rate of 1200 Hz. Finally the information is sent to an optional display. Optionally also the information could be sent to a local programmer, a remote programmer, a local or a remote patient monitor box or a remote or local server for processing, analysis, monitoring, follow up, patient management or analysis. This analysis could lead to a table of values of VV or AV delay versus activity that could be further loaded or programmed back into an implanted pacing device. Alternatively this analysis could lead to a table of values of VV or AV delays versus heart rates that could be further loaded or programmed into the device to create a rate responsive VV or AV delay setting or mode. The IEAI information could be used to help monitor the heart failure status of the patient, to help adjust drugs, such as diuretics, beta blockers or digitalis remotely by monitoring the changes they produce in the level of asynchrony.

Figure 25:
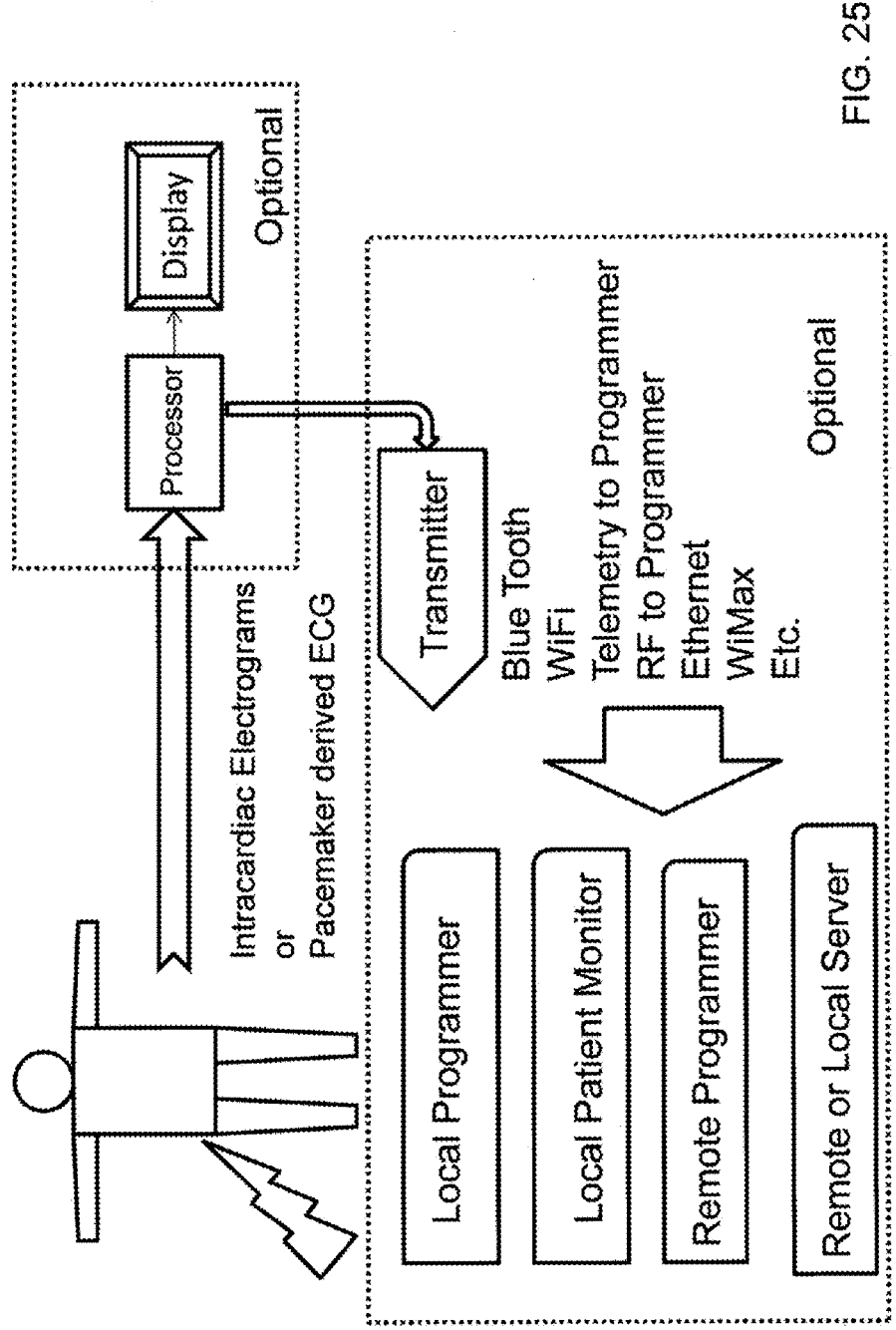
FIG. 25 shows an example block diagram where the surface ECG used in the calculation of the asynchrony index (IEAI) is derived from intracardiac electrograms available to the implanted device, and this information is transmitted to remote or local programmers, patient management or monitoring boxes or remote or local servers for further processing, analysis, monitoring or action (e.g., reoptimization of the VV delay) triggered by the local or remote systems with or without the supervision and approval of intervening medical personnel, in accordance with various aspects of the present disclosure.

FIG. 25 shows the case where the ECG information is obtained by an implanted device or by the implanted pulse generator (pacemaker, CRT or defibrillator or combination of them) and transmitted through some wireless protocol to an optional external processor and display unit or to a remote or local programmer or remote or local patient monitor box or remote of local server for further processing, analysis, use in patient management, monitoring or to provide the physician or attending medical personnel information about the changes in the asynchrony level through the IEAI obtained. Furthermore, in an embodiment of the present invention, the implanted device sends the ECG information and corresponding VV or AV value, for different values of VV or AV delay that are automatically changed in a range predefined by the responsible medical personnel, the external devices calculate the IEAI values for each VV or AV value. This information is then fed back to the responsible medical personnel and/or to the device in the form of a table or programming change that allows the device to update the VV or AV delay at which it operates when the optimum VV or AV delay is different from the one that was programmed in the last follow up, for instance due to a change in the conditions of the patient. Furthermore, this VV or AV delay changes could be made at different HR or activity levels (as measured by the rate responsive sensors the devices may have) and the information compiled in the external devices in such a way as to fed back to the responsible medical personnel and/or the device a table or programming change that allows the device to adapt the VV or AV delay with the HR and/or activity level of the patient in such a manner as to dynamically optimize the VV or AV delay.

Aspects of the present disclosure allow for the evaluation of intraventricular electrical asynchrony showing an excellent correlation with Doppler echocardiography and Tissue Doppler Imaging. It is useful for evaluating candidates for electrical resynchronization therapy to optimize the site of implantation of these devices, to improve post-implant follow-up as well as adjusting the AV and VV interval settings when programming the devices.

Various modules may be implemented to carry out one or more of the operations and activities described herein and/or shown in the Figures. In these contexts, a module (or illustrated block or box) is a circuit that carries out one or more of these or related operations/activities. For example, in certain of the above-discussed embodiments, one or more modules are discrete logic circuits or programmable logic circuits configured and arranged for implementing these operations/activities, as in the circuit modules shown in the Figures. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

In still another embodiment the implanted device calculates the IAEI using intracardiac electrical information and tracks the changes in IAEI that occur with exercise and stress, those changes are stored and their range of change established. The device then maps the range of IEAI changes with exercise to the maximum sensor rate minus the baseline heart rate programmed by the implanted physician, in such a way that when the IAEI is at the lowest bound the pacing rate is increased to the maximum sensor rate.

Based upon the above discussion and illustrations, those skilled in the art will readily recognize that various modifications and changes may be made to the present disclosure without strictly following the exemplary embodiments and applications illustrated and described herein.

What is claimed is:

1. A system for determination and utilization of cardiac electrical asynchrony data, comprising:
    an analysis circuitry comprising a processor and a memory, the processor configured to execute computer-executable code stored in the memory, the analysis circuitry configured to:
        obtain a plurality of sets of cardiac signals collected in at least two locations of a heart of a patient, the signals comprising at least one of surface electrocardiography (ECG) signals and pseudo-surface ECG signals;
        detect one or more QRS complexes for each of the sets based on the cardiac signals for that set;
        obtain one or more cross-correlation signals, each of the cross-correlation signals being between at least two of the signal sets and being obtained using the detected QRS complexes from the at least two signal sets; and
        calculate one or more asynchrony indices using one or more of the cross-correlation signals, each of the asynchrony indices being indicative of a level of asynchrony between the at least two locations.
2. A system according to claim 1, further comprising:
    an implantable stimulation device configured to apply stimulation to the patient's heart and to collect two or more of the sets of the cardiac signals while applying the stimulation.
3. A system according to claim 2, wherein one of:
    the analysis circuitry is comprised within the implantable stimulation device; and
    the implantable stimulation device wirelessly provides the at least two sets and the intervals to the analysis circuitry via a wireless circuit interfaced to the analysis circuitry.
4. A system according to claim 1, further comprising:
    an implantable stimulation device configured to cycle through a plurality of interventricular (VV) delay intervals inside a pre-determined safety range while applying stimulation to the patient's heart,
    wherein the analysis circuitry, for each of the VV delay intervals, calculates one of the asynchrony indices based on the sets of the signals associated with the stimulation applied in accordance with that interval, and determines the VV delay interval associated with a lowest one of the determined asynchrony indices as the optimal VV delay interval.
5. A system according to claim 4, wherein the stimulation comprises VVI pacing and cycling through the VV delay intervals comprises changing the stimulation in a plurality of steps from right ventricular (RV) only pacing to left ventricular (LV) pacing and one of the steps comprises applying simultaneous biventricular pacing, and the asynchrony index is calculated for the VV delay during each of the steps.
6. A system according to claim 4, wherein two of the VV delays have the lowest one of the asynchrony indices, and the analysis circuitry is further configured to:
    determine a width of an ensemble averaged QRS waveform (AAQRSC) for each of the two VV delays with the lowest asynchrony index; and
    set the VV interval with a narrowest one of the AAQRSC as the optimal VV delay interval.
7. A system according to claim 1, further comprising:
    an implantable stimulation device configured to cycle through a plurality of atrioventricular (AV) delay intervals while applying stimulation to the patient's heart in an accordance with a constant interventricular delay interval;
    an arterial pulse pressure sensor configured to measure arterial pulse pressure of the subject; and
    the analysis circuitry further configured to determine one of the AV delays as the optimal AV delay based on the arterial pulse pressure measured during the application of the stimulation in accordance with that interval.
8. A system according to claim 7, wherein the arterial pulse pressure is measured over a number of heart beats during the application of the stimulation in accordance with each of the AV intervals and the analysis circuitry is further configured to average the arterial pulse pressure for each of the intervals over the number of the beats, and the averaged pulse pressure is used for the determination of the optimal AV delay.
9. A system according to claim 8, wherein the number of the beats is defined based on user input.
10. A system according to claim 8, wherein the number of the beats comprises 8 to 64.
11. A system according to claim 7, wherein the analysis circuitry is further configured to average the arterial pulse pressure associated with each of the AV intervals over a number of respiratory cycles, and the averaged pulse pressure is used for the determination of the optimal AV delay.
12. A system according to claim 11, further comprising:
    a pulse sensor configured to monitor pulse rate and pulse amplitude of the patient;
    the analysis circuitry further configured to detect the respiratory cycles based on a modulation in the pulse rate and the pulse amplitude measured by the pulse sensor.

13. A system according to claim 7, wherein the stimulation comprises VDD and DDD pacing.

14. A system according to claim 1, further comprising:
an implantable stimulation device configured to apply stimulation to the patient's heart in accordance with a plurality of AV delays and a plurality of VV delays;
an activity sensor configured to measure a level of activity of the patient during the application of the stimulation by the implantable stimulation device in accordance with one or more of the cycled-through intervals; and
the analysis circuitry further configured to identify an optimal one of the AV delay intervals and the VV delay intervals for each of the activity levels.

15. A system according to claim 14, wherein the activity sensor comprises at least one of a minute ventilation sensor and an accelerometer.

16. A system according to claim 14, wherein the implantable device is further configured to apply the stimulation to the patient's heart in accordance with the optimal AV interval and the optimal VV intervals determined for each of the activity levels.

17. A system according to claim 1, further comprising:
an implantable stimulation device configured to apply stimulation to the patient's heart in accordance with a plurality of AV delays and a plurality of VV delays;
a heart rate sensor configured to measure a heart rate of the patient during the application of the stimulation by the implantable stimulation device in accordance with one or more of the cycled-through intervals;
the analysis circuitry further configured to:
define one or more ranges of the measured heart rate;
identify an optimal one of the AV delay intervals and an optimal one of the VV delay intervals for each of the activity levels.

18. A system according to claim 17, wherein the heart rate sensor comprises a sinus rate sensor.

19. A system according to claim 17, wherein the implantable device is further configured to apply the stimulation to the patient's heart in accordance with the optimal AV interval and the optimal VV intervals determined for each of the heart rate ranges.

20. A system according to claim 1, wherein the cardiac signals are collected using two or more electrocardiographic leads.

* * * * *